US012318524B2

(12) United States Patent
Lee, III et al.

(10) Patent No.: US 12,318,524 B2
(45) Date of Patent: Jun. 3, 2025

(54) PORTABLE PLATELET APHERESIS SYSTEM

(71) Applicant: CFD Research Corporation, Huntsville, AL (US)

(72) Inventors: Lap Man Lee, III, Madison, AL (US); Ketan Harendrakumar Bhatt, Huntsville, AL (US); Balabhaskar Prabhakarpandian, Madison, AL (US)

(73) Assignee: CFD RESEARCH CORPORATION, Huntsville, AL (US)

( * ) Notice: Subject to any disclaimer, the term of this patent is extended or adjusted under 35 U.S.C. 154(b) by 1017 days.

(21) Appl. No.: 17/313,830

(22) Filed: May 6, 2021

(65) Prior Publication Data

US 2021/0346584 A1    Nov. 11, 2021

Related U.S. Application Data

(60) Provisional application No. 63/022,180, filed on May 8, 2020.

(51) Int. Cl.
*A61M 1/34* (2006.01)
*A61M 1/36* (2006.01)
(Continued)

(52) U.S. Cl.
CPC ........ *A61M 1/3496* (2013.01); *A61M 1/3672* (2013.01); *A61M 1/38* (2013.01);
(Continued)

(58) Field of Classification Search
CPC .... A61M 1/3496; A61M 1/3672; A61M 1/38; A61M 2202/0427; A61M 2205/0244;
(Continued)

(56) References Cited

U.S. PATENT DOCUMENTS

| 8,852,446 B2 | 10/2014 | Lean et al. |
| 2013/0082012 A1* | 4/2013 | Lean ................... A61M 1/3633 210/295 |

OTHER PUBLICATIONS

Kim TH et al. "A temporary indwelling intravascular aphaeretic system for in vivo enrichment of circulating tumor cells" Nat. Commun. 10: 1478 (2019).

(Continued)

*Primary Examiner* — John Kim
(74) *Attorney, Agent, or Firm* — MASCHOFF BRENNAN

(57) ABSTRACT

A portable platelet apheresis system can include: a whole blood inlet configured to receive whole blood; an anticoagulant source containing an anticoagulant; a mixer fluidly coupled with the whole blood inlet and anticoagulant source and configured to mix the whole blood and the anticoagulant; a whole blood sorter microfluidic network; a platelet poor outlet positioned to receive a platelet poor fraction; and a platelet concentrator outlet positioned to receive a concentrated platelet fraction. The whole blood sorter microfluidic network includes: a sorter constricted region having a first cross-sectional dimension; a sorter expansion region having a second cross-sectional dimension that is larger than the first cross-sectional dimension; at least one sorter side channel (platelet rich plasma channel) formed into a side of the sorter expansion region; and at least one sorter outlet (platelet poor plasma channel) that is downstream or medial from the at least one sorter side channel.

30 Claims, 34 Drawing Sheets

(51) Int. Cl.
*A61M 1/38* (2006.01)
*B01L 3/00* (2006.01)

(52) U.S. Cl.
CPC .. *B01L 3/50215* (2013.01); *A61M 2202/0427* (2013.01); *A61M 2205/0244* (2013.01); *B01L 2200/026* (2013.01); *B01L 2300/0681* (2013.01); *B01L 2400/0409* (2013.01)

(58) Field of Classification Search
CPC .......... B01L 3/50215; B01L 2200/026; B01L 2300/0681; B01L 2400/0409
See application file for complete search history.

(56) References Cited

OTHER PUBLICATIONS

Hou HW et al. "A microfluidics approach towards high-throughput pathogen removal from blood using margination" Biomicrofluidics 6(2): 024115-024115-13 (2012).

Hou et al. "Broad spectrum immunomodulation using biomimetic blood cell margination for sepsis therapy." Lab Chip 16(4): 688-699 (2016).

Fabio Fachin et al. Monolithic Chip for High-throughput Blood Cell Depletion to Sort Rare Circulating Tumor Cells, Scientific Reports vol. 7, Article No. 10936 (2017).

\* cited by examiner

| SYRINGE | | Flow Rate (mL/min) | VALVE | | | Time (min) | Remark |
|---|---|---|---|---|---|---|---|
| A | B | | 1 | 2 | — | | |
| Prime [1] | ← | ← | 5 | ⊥ | ⊤ | ↔ | 1 | Both syringes pre-filled with 10mL saline |
| Prime [2] | ← | ← | 5 | ⊥ | ⊥ | ↔ | 2 | Filling the "RETURN" arm |
| Prime [3] | ← | → | 2 | ⊥ | ⊥ | ↕ | 2 | Filling the "EXTRACT" arm |
| Run [1] | — | ↔ | 50 | ⊥ | ⊥ | ↔ | 1 | Withdraw WB from "INL" reservoir |
| Run [2] | ↕ | ↕ | 25 | ⊤⊥ | ⊤⊥ | ↔ | [4] | Infuse/withdraw WB each cycle |
| Run [3] | ← | — | 25 | ⊥ | ⊥ | ↔ | 2 | Infuse WB for the last half cycle |

Fig. 18B

PORTABLE PLATELET APHERESIS SYSTEM

CROSS-REFERENCE TO RELATED APPLICATIONS

This patent application claims priority to U.S. Provisional Application No. 63/022,180 filed May 8, 2020, which provisional is incorporated herein by specific reference in its entirety.

U.S. GOVERNMENT RIGHTS

This invention was made with government support under N00014-18-C-7004 awarded by United States Navy and W81XWH-17-C-0177 awarded by the United States Army. The government has certain rights in the invention.

BACKGROUND

Platelet apheresis machines are configured to extract platelets (PLTs) from blood of a patient or other blood donor, and then return other blood components, such as red blood cells (RBCs) and white blood cells (WBCs), to the body. Whole blood drawn from the patient or donor is mixed with a small portion (e.g., 1:10) of anticoagulants, such as heparin or acid-citrate-dextrose (ACD), and then processed in an extracorporeal circuit of a platelet apheresis machine. Typically, a platelet apheresis machine relies on a bulk centrifugation unit (e.g., Latham bowl) for blood component fractionation. As a result, these platelet apheresis machines are usually constructed with a large footprint size and high power consumption, which prevents prior platelet apheresis machines from being miniaturized and ruggedized as a portable device. Consequently, prior platelet apheresis machines are confined to laboratories or housed spaces to accommodate the size and power requirements. Thus, the prior platelet apheresis machine technology is not suitable to be portable and deployed in the field and resource-limited environments.

An example of a prior platelet extraction system is included in U.S. Pat. No. 8,852,446, which is incorporated herein by specific reference.

Thus, there is a need for a platelet apheresis machine technology that is configured to be portable so that it can be deployed in the field and resource-limited environments.

SUMMARY

In some embodiments, a portable platelet apheresis system can include: a whole blood inlet configured to receive whole blood from a whole blood source; an anticoagulant source containing an anticoagulant; a mixer fluidly coupled with the whole blood inlet and anticoagulant source and configured to mix the whole blood and the anticoagulant; a whole blood sorter microfluidic network; a platelet poor outlet positioned to receive a platelet poor fraction; and a platelet concentrator outlet positioned to receive a concentrated platelet fraction. The whole blood sorter microfluidic network includes: a sorter constricted region having a first cross-sectional dimension; a sorter expansion region having a second cross-sectional dimension that is larger than the first cross-sectional dimension; at least one sorter side channel (platelet rich plasma channel) formed into a side of the sorter expansion region; and at least one sorter outlet (platelet poor plasma channel) that is downstream or medial from the at least one sorter side channel.

In some embodiments, a platelet concentrator is downstream from the whole blood sorter. The platelet concentrator has a platelet concentrator microfluidic network that includes: a concentrator constricted region having a third cross-sectional dimension that is fluidly coupled with the at least one sorter side channel (platelet rich plasma channel from whole blood sorter); a concentrator expansion region having a fourth cross-sectional dimension that is larger than the third cross-sectional dimension, the concentrator expansion region being downstream from the concentrator constricted region; at least one concentrator side channel (platelet poor plasma channel) formed into a side of the concentrator expansion region; and at least one concentrator outlet (platelet concentrate) that is downstream and/or medial (more central) from the at least one side channel. In some aspects, one or more central or medial concentrator outlets (e.g., outlets O3-O7) are between the platelet concentrate concentrator outlet (two main outlets). When the concentrator side channels are the ultimate channels (O1 and O9, from the middle), then the concentrator outlet for platelet concentrate are the penultimate channels (O2 and O8). Any antepenultimate channels inward towards the middle from the concentrator side channels (O7-O3) are the ultimate channels (from the middle) can also be used to obtain platelets in a lesser concentrate than the platelet concentrate.

In some embodiments, the platelet poor outlet is fluidly coupled with the at least one sorter outlet (e.g., medial, penultimate and antepenultimate in sorter)) and/or the at least one concentrator side channel (e.g., ultimate in concentrator). In some aspects, the platelet concentrator outlet is fluidly coupled with the at least one concentrator outlet (e.g., penultimate in concentrator).

In some embodiments, the whole blood sorter is included on a microfluidic cartridge, which can be removably fluidly coupled with the outlet of the mixer, wherein the microfluidic cartridge includes the whole blood sorter, wherein the whole blood sorter has the whole blood sorter microfluidic network. The cartridge is removable and replaceable in the portable platelet apheresis system. The cartridge can be disposable or cleanable for reuse (e.g., cleaned with a cleaning protocol with water with or without detergent).

In some embodiments, the system can include a platelet concentrator downstream from the whole blood sorter. The platelet concentrator has a platelet concentrator microfluidic network that includes: a constricted region having a first cross-sectional dimension; an expansion region having a second cross-sectional dimension that is larger than the first cross-sectional dimension; at least one side channel formed into a side of the expansion region; and at least one outlet that is downstream or medial from the at least one side channel. In some aspects, the platelet concentrator microfluidic network includes: a concentrator constricted region having a third cross-sectional dimension; a concentrator expansion region having a fourth cross-sectional dimension that is larger than the third cross-sectional dimension; at least one concentrator side channel formed into a side of the concentrator expansion region; at least one concentrator outlet that is downstream or medial from the at least one side channel; a platelet poor outlet fluidly coupled with the at least one concentrator side channel (e.g., ultimate from central line); and a platelet concentrator outlet fluidly coupled with the at least one concentrator outlet (e.g., penultimate from central line).

In some embodiments, the whole blood sorter microfluidic network and platelet concentrator microfluidic network are in the same cartridge or different cartridges. In some aspects, the sorter microfluidic network is in a sorter body of the cartridge and the platelet concentrator microfluidic network are in a concentrator body of the same cartridge. In some aspects, the sorter microfluidic network is in a first body of the cartridge and the platelet concentrator microfluidic network are in a second body of the same cartridge, and the cartridge includes an intermediate body with microfluidic channels that fluidly couple the sorter microfluidic network with the concentrator microfluidic network.

In some embodiments, the system includes a pump fluidly coupled to the mixer and microfluidic network and a microcontroller operably coupled to the pump that is fluidly coupled to the mixer and microfluidic network.

In some embodiments, the system can include one or more of: a casing containing the components of the portable platelet apheresis system; a pump fluidly coupled to the mixer and microfluidic network; a port in the casing adapted for removably receiving the cartridge; a flowmeter fluidly coupled with a pump and the cartridge; and micro-controller that is configured to receive flow date from the flowmeter and provide flow rate instruction data to the pump to obtain a desired flow rate.

In some embodiments, the system includes: a series of whole blood sorter microfluidic networks (in sequence); and at least one concentrator microfluidic network downstream from at least one (or all) of the whole blood sorter microfluidic networks. A concentrator can be downstream from one or more of the sorters.

In some embodiments, the system includes: a series of whole blood sorter microfluidic networks in series; and at least one concentrator microfluidic network downstream from each of the whole blood sorter microfluidic networks. In some aspects, the system can include a saline source fluidly coupled with an inlet of the sorter constricted region of a first whole blood sorter microfluidic network. In some aspects, the system includes: a series of whole blood sorter microfluidic networks in series; and one concentrator microfluidic network downstream from a last whole blood sorter microfluidic network of the series.

In some embodiments, a whole blood sorter can include a whole blood sorter microfluidic network that includes: an inlet; a sorter constricted region having a first cross-sectional dimension downstream of the inlet; a sorter expansion region having a second cross-sectional dimension that is larger than the first cross-sectional dimension and that is downstream of the sorter constricted region; at least one sorter side channel formed into a side of the sorter expansion region; and at least one sorter outlet that is downstream or medial/central from the at least one side channel In some aspects, the inlet is configured to include whole blood, the expansion region is configured to include platelets preferentially in side lateral regions thereof and include white blood cells and red blood cells preferentially in a medial region between the two side lateral regions. In some aspects, during use at least one sorter side channel includes a majority of separated platelets and a minority of separated white blood cells and separated red blood cells. In some aspects, during use at least one sorter outlet includes a majority of separated white blood cells and separated red blood cells and a minority of separated platelets.

In some embodiments, the whole blood sorter can include: two sorter side channels formed into opposite sides of the sorter expansion region; and at least one sorter outlet are arranged laterally between the two sorter side channels. In some aspects, the whole blood sorter includes an inlet narrowing taper region upstream of the sorter constricted region. In some aspects, the whole blood sorter expansion region includes an expanding section with a narrow inlet and expanded outlet. In some aspects, the whole blood sorter expansion region includes an expanding section with a narrow inlet and expanded outlet upstream of the constricted section.

In some embodiments, the whole blood sorter can include two sorter side channels formed into opposite sides of the sorter expansion region and being outer channels, and a plurality of sorter outlets all arranged laterally between the two sorter side channels and being inner channels between the two outer channels. In some aspects, the whole blood sorter can include two sorter side channels that are at opposite corners of a square, rectangle, or triangle shaped expansion region with the plurality of sorter outlets all arranged at the base of a triangle shaped expansion region between the opposite corners.

In some embodiments, a platelet concentrator can include a platelet concentrator microfluidic network that includes: an inlet; a concentrator constricted region having a first cross-sectional dimension downstream of the inlet; a concentrator expansion region having a second cross-sectional dimension that is larger than the first cross-sectional dimension and that is downstream of the concentrator constricted region; at least one concentrated side channel formed into a side of the concentrator expansion region; and at least one concentrator outlet that is downstream or medial/central from the at least one side channel In some aspects, the inlet is configured to include platelet rich plasma during use. In some aspects, the expansion region is configured to include plasma preferentially in side lateral regions thereof during use, and includes platelets preferentially in a medial region between the two side lateral regions during use. In some aspects, the at least one concentrator side channel includes a majority of plasma and a minority of separated platelets during use. In some aspects, the at least one concentrator outlet includes a majority of separated platelets during use.

In some embodiments, the platelet concentrator can include: two sorter concentrator channels formed into opposite sides of the concentrator expansion region; and at least one concentrator outlet arranged laterally between the two concentrator side channels. In some aspects, the platelet concentrator can include an inlet narrowing taper region upstream of the concentrator constricted region. In some aspects, the concentrator expansion region includes an expanding section with a narrow inlet and expanded outlet upstream of the concentrator constricted region.

In some embodiments, the platelet concentrator includes two concentrator side channels formed into opposite sides of the concentrator expansion region and being outer channels, and a plurality of concentrator outlets all arranged laterally between the two concentrator side channels and being inner/central channels between the two outer channels. In some aspects, the two concentrator side channels are at opposite corners of the triangle or rectangle (or square) shaped expansion region with the plurality of concentrator outlets all arranged at the base of a triangle or rectangle shaped expansion region between the opposite corners.

In some embodiments, a method of separating platelets from whole blood can include: providing the portable platelet system of one of the embodiments; introducing whole blood into the whole blood inlet; mixing the whole blood with the anticoagulant; introducing the whole blood from the mixer into the whole blood sorter; collecting separated platelets from at least one sorter side channel and/or at least one concentrator outlet; and collecting separated white blood cells and red blood cells from at least one sorter outlet. In some aspects, the method includes collecting platelet poor plasma from the at least one concentrator side channel In some aspects, the method includes controlling a flow rate through the microfluidic networks.

In some embodiments, a method of separating platelets from whole blood can include: proving the whole blood sorter of one of the embodiments; introducing whole blood into the sorter constricted region; flowing the whole blood through the sorter expansion region so as to preferentially distribute platelets at lateral sides and preferentially distribute white blood cells and red blood cells medially between the lateral sides; collecting separated platelets from the at least one sorter side channel; and collecting separated white blood cells and red blood cells from the at least one sorter outlet. In some aspects, the method includes controlling a flow rate through the microfluidic networks.

In some embodiments, a method of separating platelets from platelet rich plasma can include: proving the platelet concentrator of one of the embodiments; introducing platelet rich plasma into the concentrator constricted region; flowing the platelet rich plasma through the constrictor expansion region so as to preferentially distribute platelets away from the lateral sides and preferentially distribute platelets medially between the lateral sides; collecting separated platelet poor plasma (PPP) from the at least one side channel; and collecting separated platelets (platelet concentrate, PC) from the at least one outlet downstream or medial/central from the side channels. In some aspects, the method includes controlling a flow rate through the microfluidic networks. The side outlets of the separator lack blood cells. The side outlets thereby preferentially receive plasma that is devoid of or has significantly less live cells (not platelets, which are not live cells) compared to the downstream outlet or medial/central outlet.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 18B shows valve actuation steps for the different processing steps: priming, and running, which can be controlled by the computing device of FIG. 13.

Figure 1:
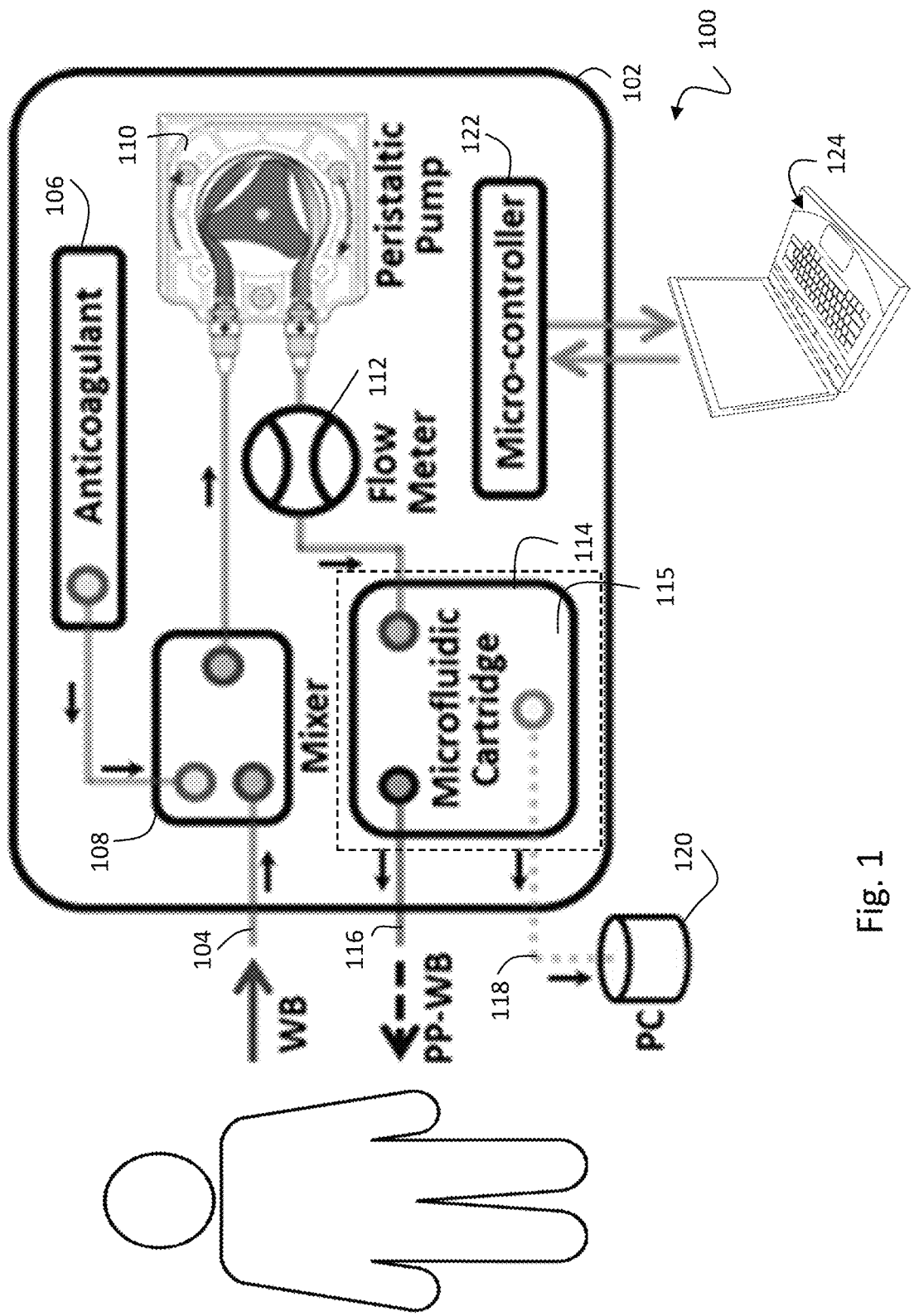
FIG. 1 illustrates an example of an embodiment of a portable apheresis system.

The elements and components in the figures can be arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology includes a portable platelet apheresis machine that is rugged and stable so that it can be moved between locations and used in the field or on site. The machine includes a casing that is the size of a briefcase or luggage that can be handheld. The portable platelet apheresis machine can be configured to be operated by an external power supply or batteries with significantly less power consumption than prior machines. The lower power consumption arises at least in part from replacing the bulk centrifugation unit with a smaller microfluidic cartridge, which can be configured as a consumable or single use item (e.g., disposable). The microfluidic cartridge can be operated with significantly less power compared to a centrifuge (e.g., Latham bowl). Thus, the portable platelet apheresis machine can use a microfluidic cartridge for blood component fractionation.

In some embodiments, the present technology includes a microfluidic cartridge that operates in a portable platelet apheresis system. The cartridge is configured to sort whole blood and then to concentrate platelets. In some aspects, the portable platelet apheresis system includes: a whole blood inlet configured to receive whole blood from a whole blood source; an anticoagulant source containing an anticoagulant; a mixer fluidly coupled with the whole blood inlet and anticoagulant source and configured to mix the whole blood and the anticoagulant; and a whole blood sorter microfluidic network. The whole blood sorter microfluidic network that includes: a sorter constricted region having a first cross-sectional dimension; a sorter expansion region having a second cross-sectional dimension that is larger than the first cross-sectional dimension; at least one sorter side channel formed into a side of the sorter expansion region; and at least one sorter outlet that is downstream or medial from the at least one side channel.

In some embodiments, the portable platelet apheresis system also includes a platelet concentrator downstream from the whole blood sorter. In some aspects, the platelet concentrator has a platelet concentrator microfluidic network that includes: a constricted region having a first cross-sectional dimension; an expansion region having a second cross-sectional dimension that is larger than the first cross-sectional dimension; at least one sorter side channel formed into a side of the sorter expansion region; and at least one sorter outlet that is downstream or medial/central from the at least one side channel. The platelet concentrator microfluidic network can include: a concentrator constricted region having a third cross-sectional dimension; a concentrator expansion region having a fourth cross-sectional dimension that is larger than the third cross-sectional dimension; at least one concentrator side channel formed into a side of the concentrator expansion region; and at least one concentrator outlet that is downstream or medial from the at least one side channel In some aspects, the portable platelet apheresis system also includes: a platelet poor outlet fluidly coupled with the at least one sorter outlet and/or the at least one concentrator side channel; and a platelet concentrator outlet fluidly coupled with the at least one concentrator outlet.

The portable platelet apheresis system can have various configurations. FIG. 1 illustrates an example of an embodiment of a portable apheresis system. The system can include an outflow from a donor into the portable platelet apheresis device 100, which includes a housing 102 retaining an inlet 104, anticoagulant source 106, mixer 108 configured to mix the blood from the inlet 104 with the anticoagulant from the anticoagulant source 106, peristaltic pump 110, flow meter 112, and microfluidic cartridge 114 (e.g., removable, such as through a port 115) that includes an outlet 116 to the donor in-flow and an outlet 118 to the platelet collector 120 ("PC"). Also, a microcontroller 122 is shown, which can be connected to a computer 124 or any input/output device. In some aspects, the microcontroller 122 is a computer.

In some embodiments, the portable platelet apheresis machine omits or is otherwise devoid of a centrifuge or Latham bowl, or other mechanical separation device that applies a mechanical force for separation of blood components.

In some embodiments, the portable platelet apheresis machine can include at least one microfluidic channel network having a main channel with an inlet and a conduit between at least two outlets, where at least one outlet is a side channel outlet extending from a side wall of a main channel. The microfluidic channel network can be configured as illustrated in in the figures or as described herein. The microfluidic channel network can be included in a cartridge, which can be configured to be removable and disposable as a single use consumable. The microfluidic channel network can receive undiluted blood combined with a small amount of anticoagulant, which is processed in the microfluidic cartridge in a high-throughput and high processing capacity. For example, the microfluidic cartridge can process blood at a volume flow rate about 20 mL/min, or from about 15 mL/min to about 25 mL/min, or from about 10 mL/min to about 50 mL/min, or other configurable volume flow rates as needed or desired. The length of the conduit between the inlet and at least first outlet can be modified as needed or desired.

In some embodiments, the microfluidic cartridge can be configured to be connected and interfaced with a closed loop fluidic operation system. An example of such a closed loop fluidic operation system is shown in FIG. 1. The volume flow rate can be driven with a peristaltic pump (FIG. 1) or a syringe pump, continuous pump, or any other pump, such as those capable of closed loop operation.

In some embodiments, the microfluidic cartridge consumable can include a whole blood (WB) sorter component and a platelet (PLT) concentrator component. The WB sorter and PLT concentrator can include microfluidic channels or networks housed in a cartridge housing, each with an inlet and at least two outlets.

Figure 2A:
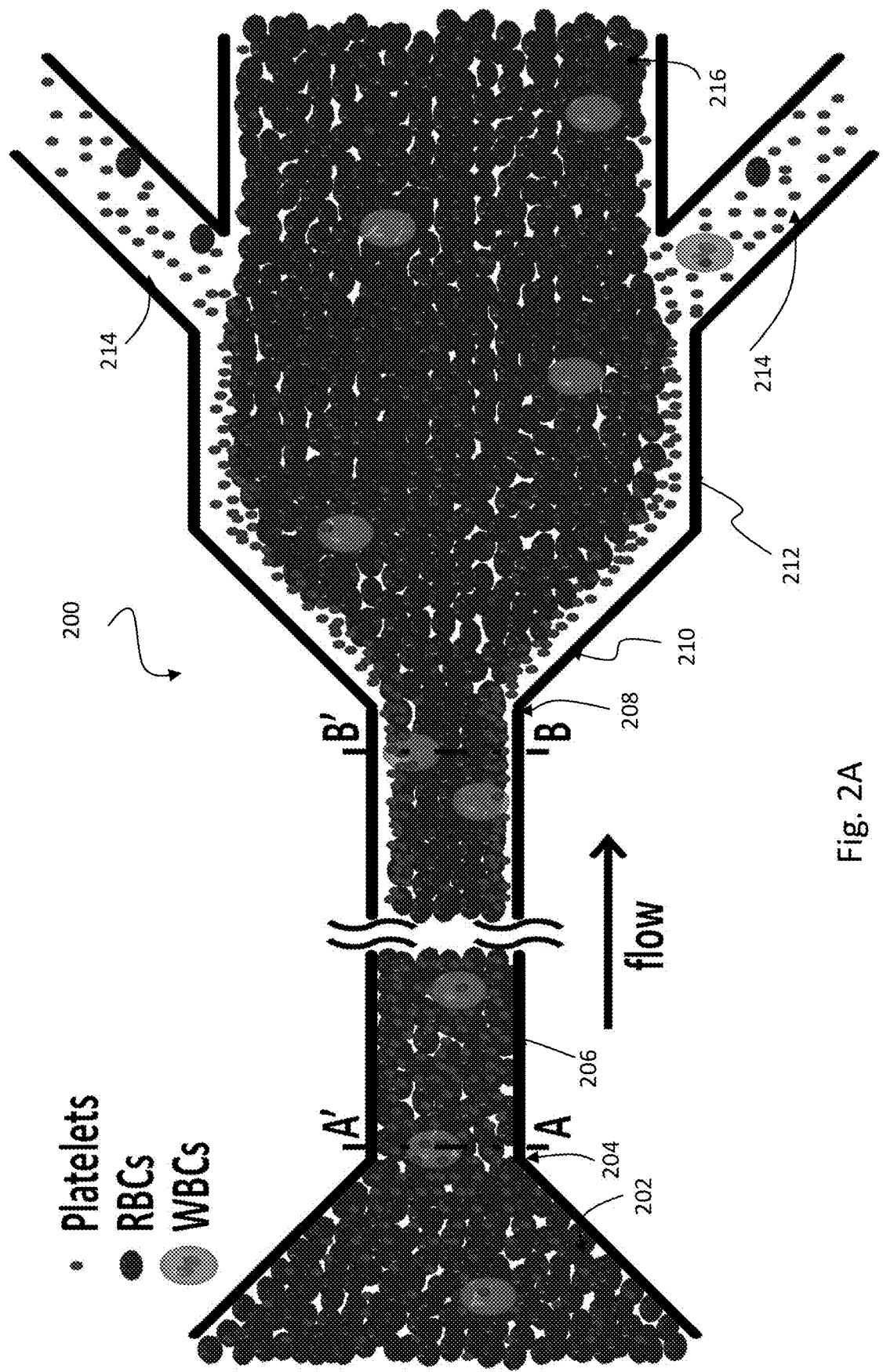
FIG. 2A is a top view or longitudinally oriented cross-sectional view of the platelet separator channel that can be used for the whole blood sorter and the platelet concentrator.
Figure 2B:
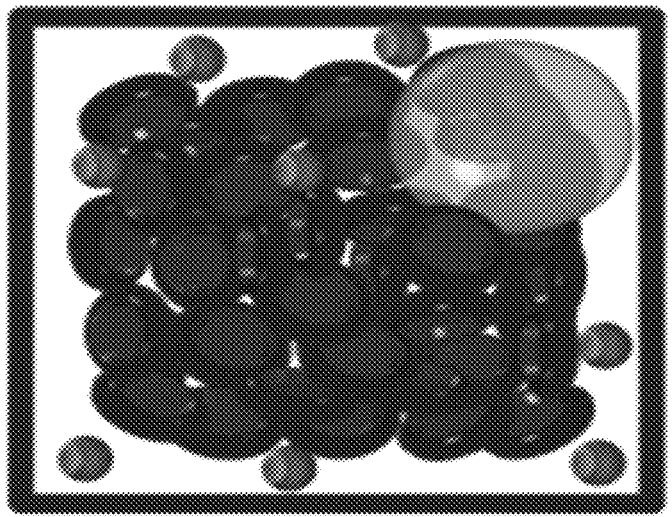
FIG. 2B includes two cross-sectional views (laterally oriented) of the platelet separator channel of FIG. 2A at A-A' and B-B'.
Figure 2B:
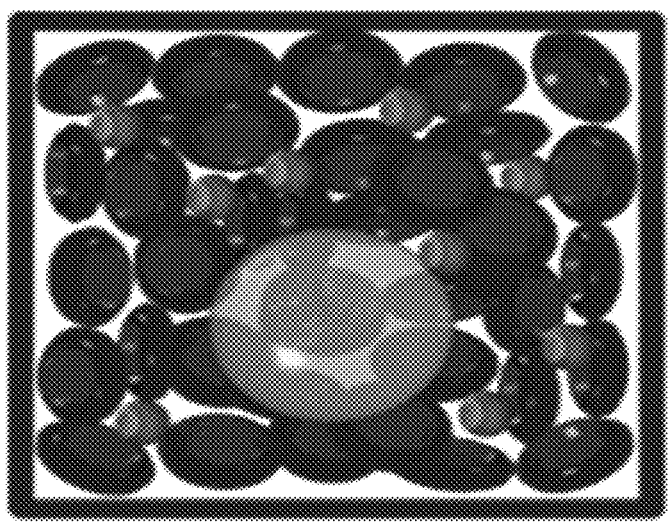

FIGS. 2A-2B illustrates a schematic illustration of platelet separator channel 200 to provide a demonstration of platelet margination of whole blood in a constricted microfluidic channel. FIG. 2A is a top view or longitudinally oriented cross-sectional view of the platelet separator channel 200. FIG. 2B includes two cross-sectional views (laterally oriented) of the platelet separator channel 200 at A-A' and B-B'. The platelet separator channel includes a narrowing tapered region 202 having a narrowed outlet 204 fluidly coupled to and/or includes of a constricted region 206. The constricted region 206 extends to a constricted outlet 208 that is fluidly coupled with an expansion region 210, which expands the dimension of the channel. The expansion region 210 is shown to have an expanded region 212 extending therefrom. The expanded region 212 includes at least one side channel outlet 214, where two side channel outlets 214 are shown, but more may be included. However, the side channel outlets may be included in the expansion inverse tapered region 210. The expansion region 212 includes at least one downstream outlet 216 downstream from the at least one side channel outlet 214, which at least one downstream outlet 216 can have the dimension of the expanded region 212 or divided into a plurality of downstream outlets. For example, the downstream outlets can be at the centerline axis as the main channel outlet.

The WB sorter unit can include a straight constricted microfluidic channel followed by an expansion microfluidic channel having at least two exits. The microfluidic channels can have various cross-sectional dimensions at the constricted region and the expansion region as shown in FIG. 2A. For example, the constricted region can include a cross-sectional dimension of at least about 20 microns, or from about 20 microns to about 100 microns, but could be larger if needed or desired (e.g., 200, 300, or up to 500 microns). The expansion region can be at least 1.2 times larger than the constricted region, or at least about 1.5 times, or at least about 2 times, or at least about 3 times, or at least about 4 times larger than the constricted region. The constricted region can be a dimension of tens of microns, and an expansion feature is located close to the channel outlet. During use, the undiluted whole blood (WB) is injected into the constricted microfluidic channel and passed through the expansion region. The smaller and rigid PLTs (e.g., 2-3 µm) are preferentially distributed near the lumen surface (e.g., marginated or moved to the margins) to form a cell-free layer (CFL) near the side walls of the constricted region, which can be due to the intense interaction with larger deformable RBCs (e.g., 5-7 µm). FIGS. 2A-2B show the smaller PLTs in a random distribution throughout the cross-section near the inlet and then preferentially distributed at the lumen surface.

FIG. 2B shows the distribution of the platelets (PLTs), red blood cells (RBCs), and white blood cells (WBCs) at the inlet (near inlet) and outlet (near outlet) of the constriction region. In the expansion region, the PLTs are preferentially dispersed to the outside of the channel so as to be near the lumen surface. This allows for marginated PLTs to be collected by two side PRP (platelet-rich plasma) side channel outlets, as shown in FIG. 2A. However, it should be recognized that only one PRP side channel may be used, or any number of side channels can extend from the expansion region. Most RBCs migrate towards the channel axial centerline. Accordingly, the RBCs are collected by the center outlet (e.g., return outlet) and then routed to return to the blood donor. Additionally, most WBCs (e.g., 7-15 µm) are collected in the center outlet channel and returned to the donor.

The constricted region of the microfluidic channel can be considered to be an inlet into the WB sorter unit. The expansion region and the PRP side channel outlets (e.g., channels that are outlets from the expansion region) can be upstream from and fluidly coupled to a PLT concentrator unit. As such, the PLT concentrator unit is downstream from the WB sorter unit.

In some embodiments, to increase PLT extraction/collection efficiency, several constriction channel/expansion features can be arranged in serial configuration in the WB sorter. Optimized sorting and recovery performance can be achieved by balancing the fluidic resistance at each "PRP" side channel outlet and each "return" outlet channel.

In some embodiments, one or more PLT concentrators are connected directly with each WB sorter unit in serial configuration, from the sorter side channels. To increase the throughput rate of the microfluidic cartridge for platelet apheresis, typically on the order of 20 mL/min to 100 mL/min, multiple serial WB sorter channel networks and PLT concentrator channels can be arranged in parallel, such as in a radial configuration. Each radial WB sorter channel network and PLT concentrator channel network can be configured as plates that can be stacked up to further increase the throughput. As noted, each concentrator inlet is coupled to a sorter side channel to obtain the platelets.

In some embodiments, the microfluidic cartridge (e.g., consumable cartridge) can be fabricated with injection molding. The microfluidic cartridge can be configured as microfluidic disk, which can be made of medical-grade cyclic olefin copolymer (COC) or any other polymer materials and manufactured using direct laser writing mastering in combination with variothermal (localized time-dependent temperature control) injection-compression molding.

In some embodiments, the inlets and/or outlets of the microfluidic network can be fabricated on the lid layer of the cartridge, and laser welded with the molded COC on-chip-cassette. Disposable tubing and fluidic connections of the microfluidic cartridge can be fitted to various microfluidic sub-components of the automated processing apparatus.

WB Sorter Unit (Single Pass)

As indicated above, FIGS. 2A-2B illustrates a schematic illustration of platelet separator channel 200 to provide a demonstration of platelet margination of whole blood in a constricted microfluidic channel. FIG. 2A is a top view or longitudinally oriented cross-sectional view of the platelet separator channel 200. FIG. 2B is cross-sectional view (laterally oriented) of the platelet separator channel 200. For example, the downstream outlets can be at the centerline axis as the main channel outlet.

In some embodiments, the microfluidic network can have a high aspect ratio (HAR) straight microfluidic channel, which can be used for PLT margination for WB samples. The microfluidic device can include a small focusing channel (e.g., 8 mm×20 μm×50 μm (L×W×H), which can have a 30° gradual expansion (e.g., range can be from 30 degrees expansion to 90 degrees expansion) collection channel, and at least one side channel outlet (e.g., 9 side channel outlets). Each side channel outlet can include a cross-dimension of about 100 μm in width.

Figure 3A:
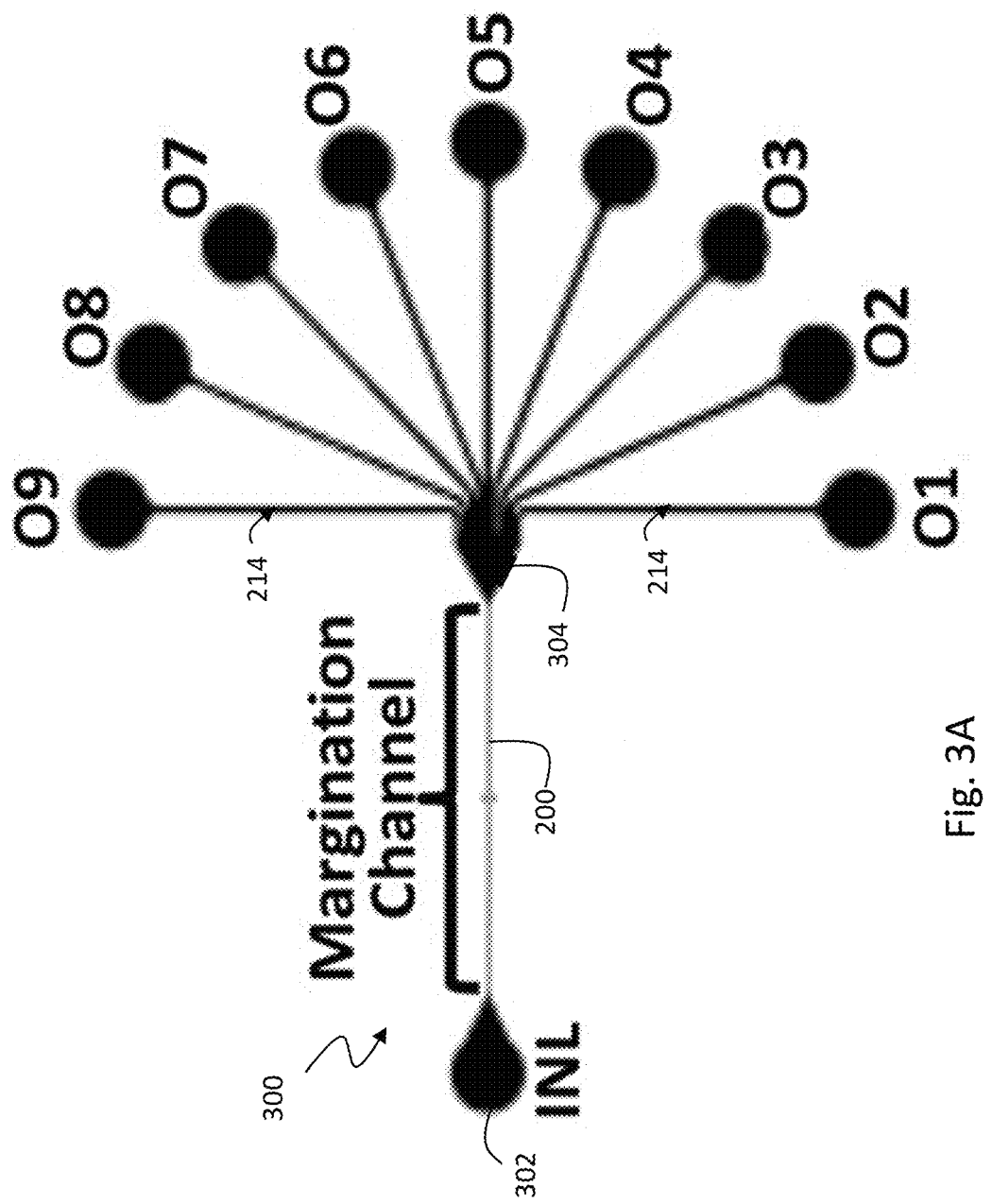
FIG. 3A shows an embodiment of a microfluidic network having the inlet (INL), platelet margination channel with the outlet expansion channel (e.g., expanded region) with a plurality of side channels (e.g., side channels O1, O2, O3, O4, O5, O6, O7, O8, and O9).

FIG. 3A shows an embodiment of a microfluidic network 300 having the inlet 302 (INL), platelet margination channel 200 with the outlet expansion channel 304 (e.g., expanded region 212) with a plurality of side channels 214 (e.g., side channels O1, O2, O3, O4, O5, O6, O7, O8, and O9); however, more or less side channels may be used.

Figure 3B:
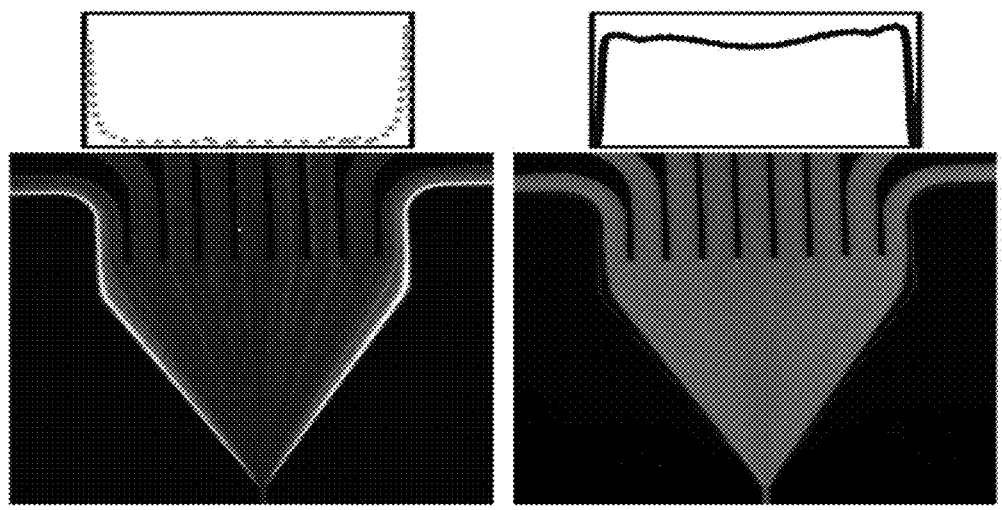
FIG. 3B shows the margination of Calcein AM stained PLTs in the expansion channel at flow rate ranging from 20 μL/min to 80 μL/min.
Figure 3B:
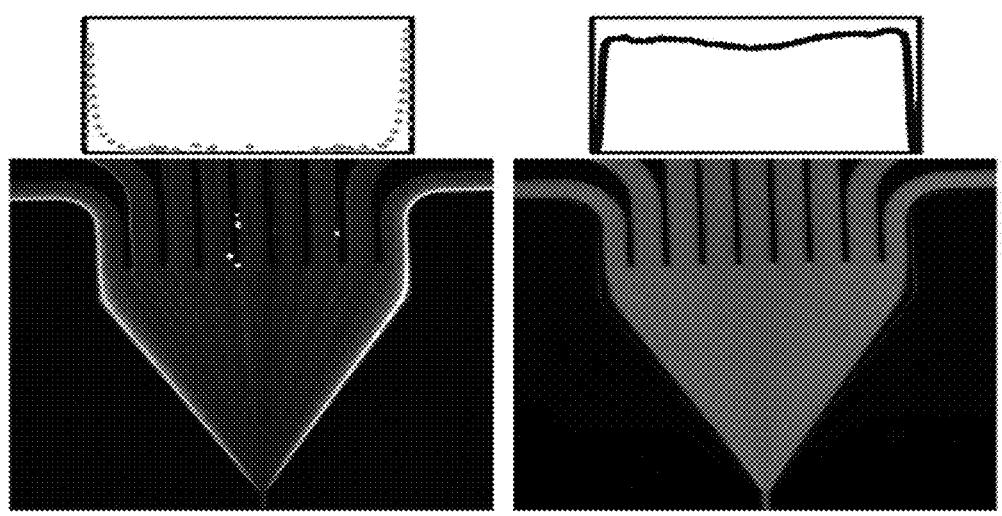
Figure 3B:
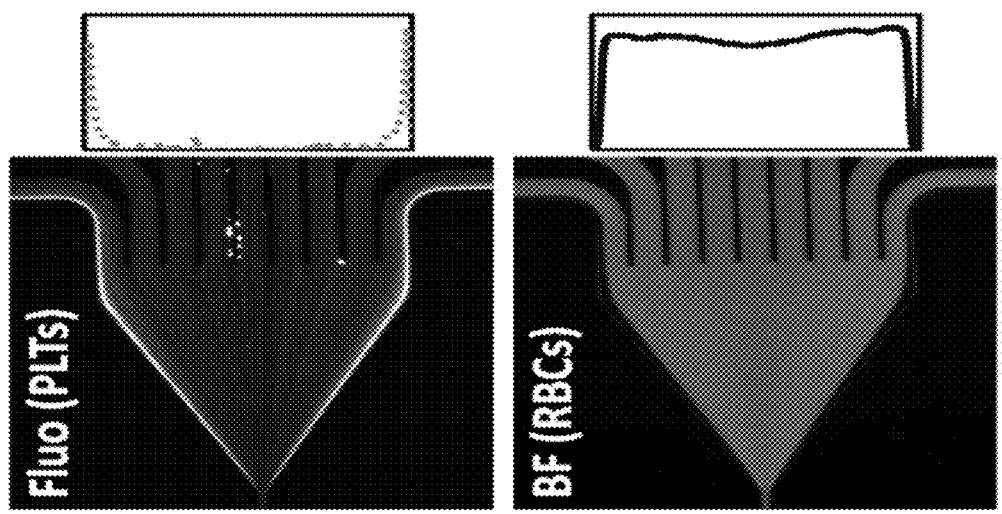

To enable visualization of PLT migration, purified and fluorescently labeled human PLTs with Calcein AM were prepared. The Calcein AM stained PLT pellet was re-suspended in original PPP and mixed with stored RBCs to replicate the initial whole blood cell counts and concentration. FIG. 3B shows the margination of Calcein AM stained PLTs in the expansion channel at flow rate ranging from 20 μL/min to 80 μL/min. At flow rate of 20 μL/min (Re ~3), RBCs experience high shear and inertia in the focusing channel which facilitate their migration to the channel centerline, while the smaller and rigid PLTs are marginated towards the channel side walls. In the outlet expansion channel, two tightly marginated PLT flow trajectories formed in proximity with the expanded CFL region were collected in outlets O1 and O9 as shown in FIG. 3A. Due to their high concentration, the RBCs trajectories spanned across outlets O1-O9, leaving a small portion of CFL region near the side wall of outlets O1 and O9. The fluorescence and bright field intensity profiles were plotted next to the experiment flow trajectories images at each flow rate. When increasing the flow rate up to 200 μL/min (Re ~31), similar flow trajectories and intensity profiles were observed at different flow rates.

Figure 3C:
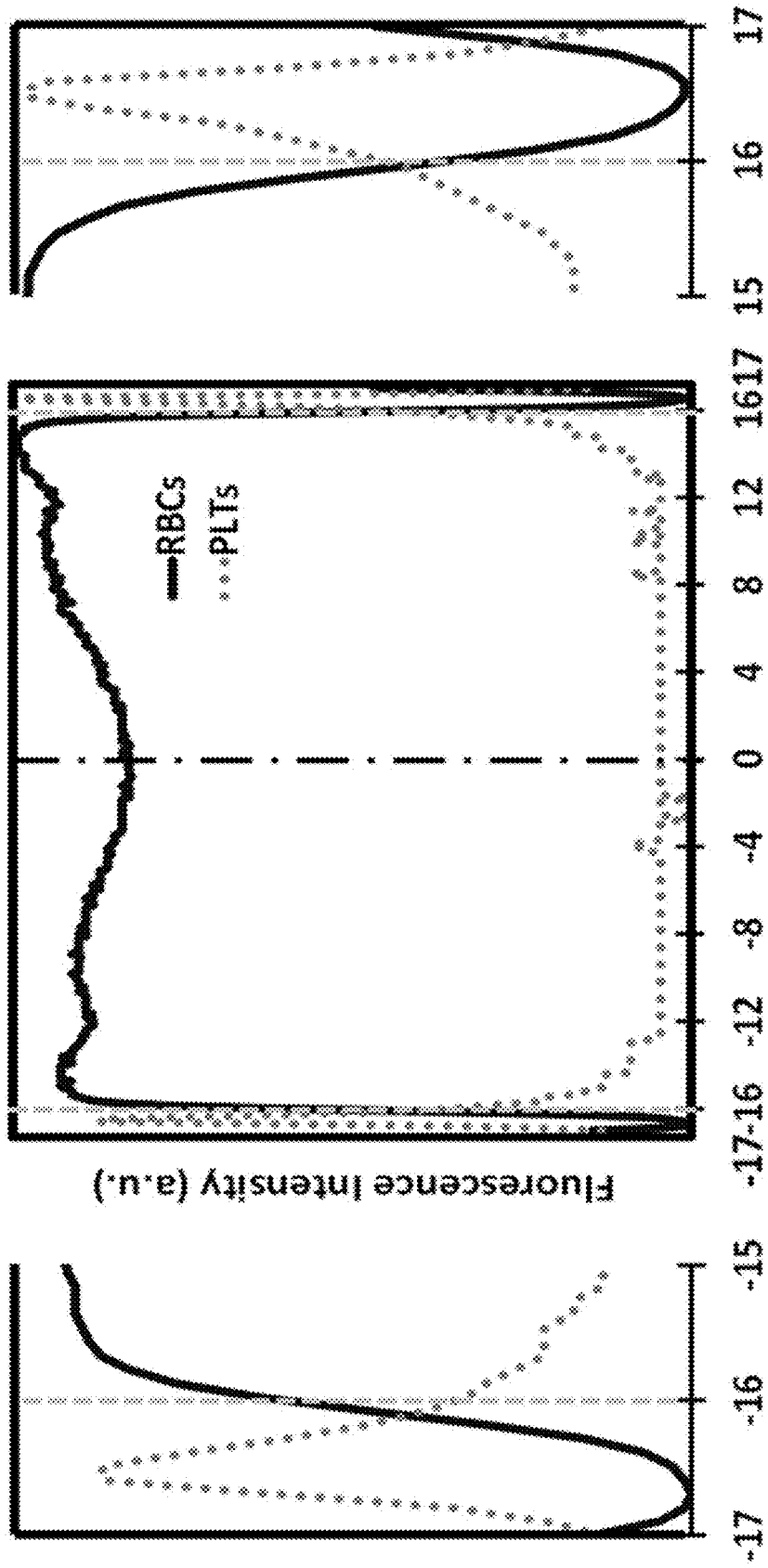
FIG. 3C shows an intensity profiles at 80 μL/min (Dotted line—Intensity profile for PLTs acquired using fluorescence imaging; Solid Line—Intensity profile for RBCs acquired using bright-field imaging).

FIGS. 3A-3C demonstrate PLT margination in WB samples with a high aspect ratio (HAR) straight microfluidic channel. FIG. 3A shows a schematic of the system. FIG. 3B shows the PLT collection at different flow rates (Fluo— Fluorescent imaging of stained PLTs; BF—Bright-field imaging of RBCs). FIG. 3C shows intensity profiles at 80 μL/min (Dotted line—Intensity profile for PLTs acquired using fluorescence imaging; Solid Line—Intensity profile for RBCs acquired using bright-field imaging).

To demonstrate and characterize performance in WB sorting and PLT extraction in constricted the HAR microfluidic channel using samples collected "off-chip", outlet fluidic resistance of the high aspect ratio straight channel device is manipulated to optimize for RBC and PLT recoveries for high PLT purity. Examination of the fluorescence (PLTs) and bright field (RBCs) intensity profiles at volume flow rate of Q=80 μL/min, found that the optimal volume flow ratio between outlets "PRP" (outlets O1 and O9) and "RBC Return" (outlets O2-O8) recovery is about 1:17 (FIG. 3C), which allows a considerable amount of PLTs to be extracted in outlets O1 and O9, and a majority of RBCs (>99.9%) to be recovered in the "return" outlet (outlets O2-O8).

Figure 4:
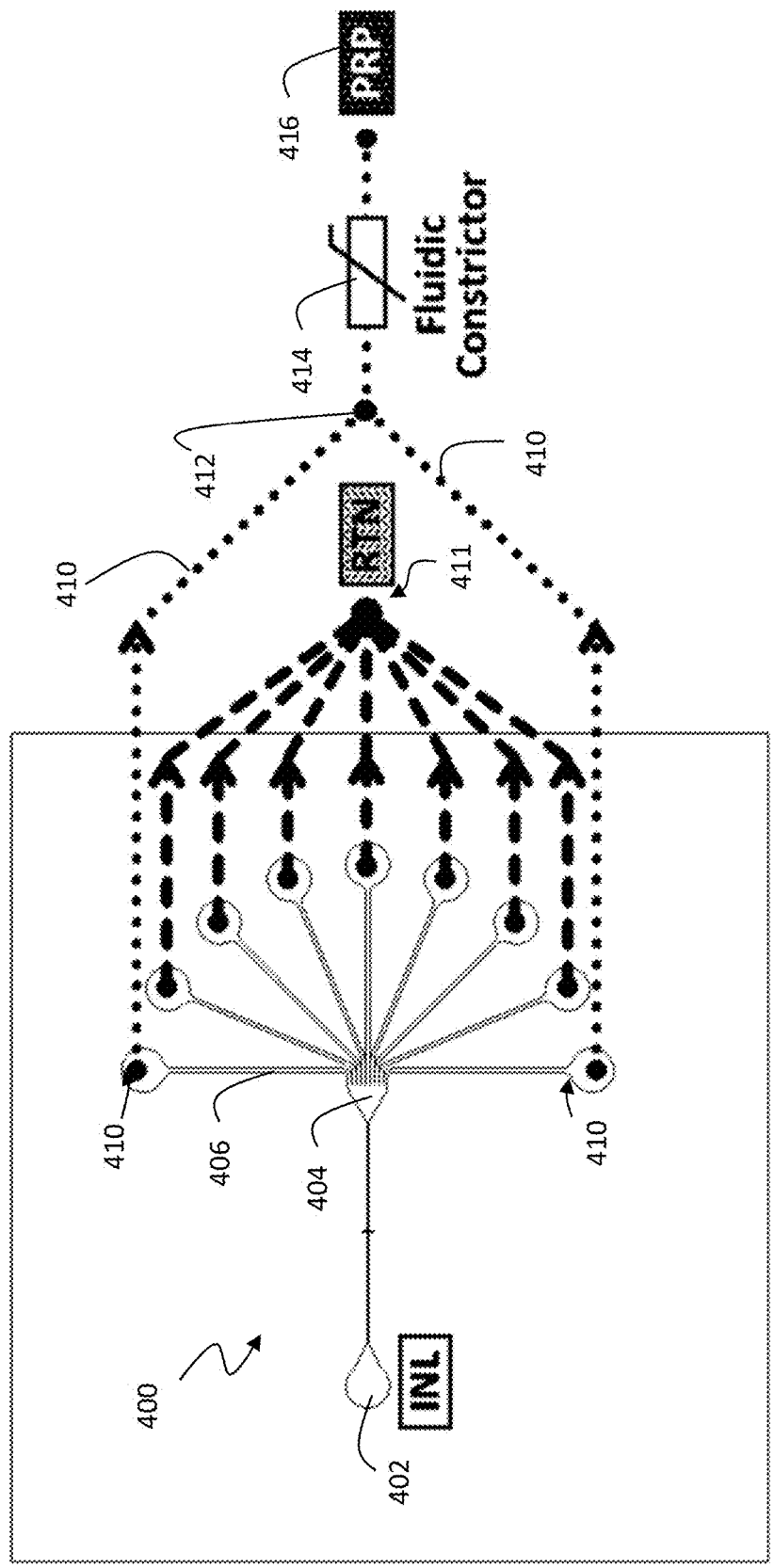
FIG. 4 shows the schematic of the whole blood sorter for PLT extraction with HAR straight microfluidic channel.

Additionally, the system can be formed to include the HAR microfluidic device coupled with other microfluidic devices that allow for achieving the desired fluidic resistance necessary for optimal separation of platelets and RBCs (see FIG. 4). The outlets O2-O8 of the high aspect ratio (HAR) straight microfluidic channel were grouped together as a return (e.g., RTN 411) to the patient (e.g., to patient inflow, outlet 116). The outlets for the PRP (e.g., outlets O1 and O9) of the HAR microfluidic channel were combined and connected to microfluidic devices (e.g., 1.5 cm dimension) connected to two inlets (e.g., 410) of a bifurcation channel (BIF) device. In an example, the BIF microfluidic device includes one parent 412 and two daughter channels 410. In an example, the width of parent channel and daughter channels are 100 μm and 50 μm respectively, but can vary (e.g., 5%, 25%, 50%). Both parent and daughter channels can have a constant height (e.g., 50 μm). The outlet of the BIF microfluidic channel (e.g., parent 412) can be connected to the inlet of the linear channel (LC) microfluidic device. However, one, two, or more than three straight channels can be used. By connecting the microfluidic devices in series, the expected fluidic resistance between "PRP" and "Return" outlets was achieved as 1:17.5.

FIG. 4 shows the schematic of the WB sorter 400 for PLT extraction with HAR straight microfluidic channel PRP outlets were connected to 3× linear channels with length of 1.5 cm each and cross-section of 100 μm×100 μm. This microfluidic assembly is constructed to manipulate for fluidic resistance to optimize for RBC and PLT recoveries. In another example, freshly acquired WB sample is injected into the microfluidic module (FIG. 4) at a volume flow rate of 80 μL/min.

FIG. 4 shows the WB sorter 400 includes the inlet 402 (INL) that feeds into a separator region 404 that has the arranged outlet lines 406 that correspond with outlets O1 through O9 (as defined herein). The outlet lines 406 of O1 and O9 outlets go to a mixer 412 that feeds into a fluidic constrictor 414 to obtain the platelet rich portion 416.

Figure 5A:
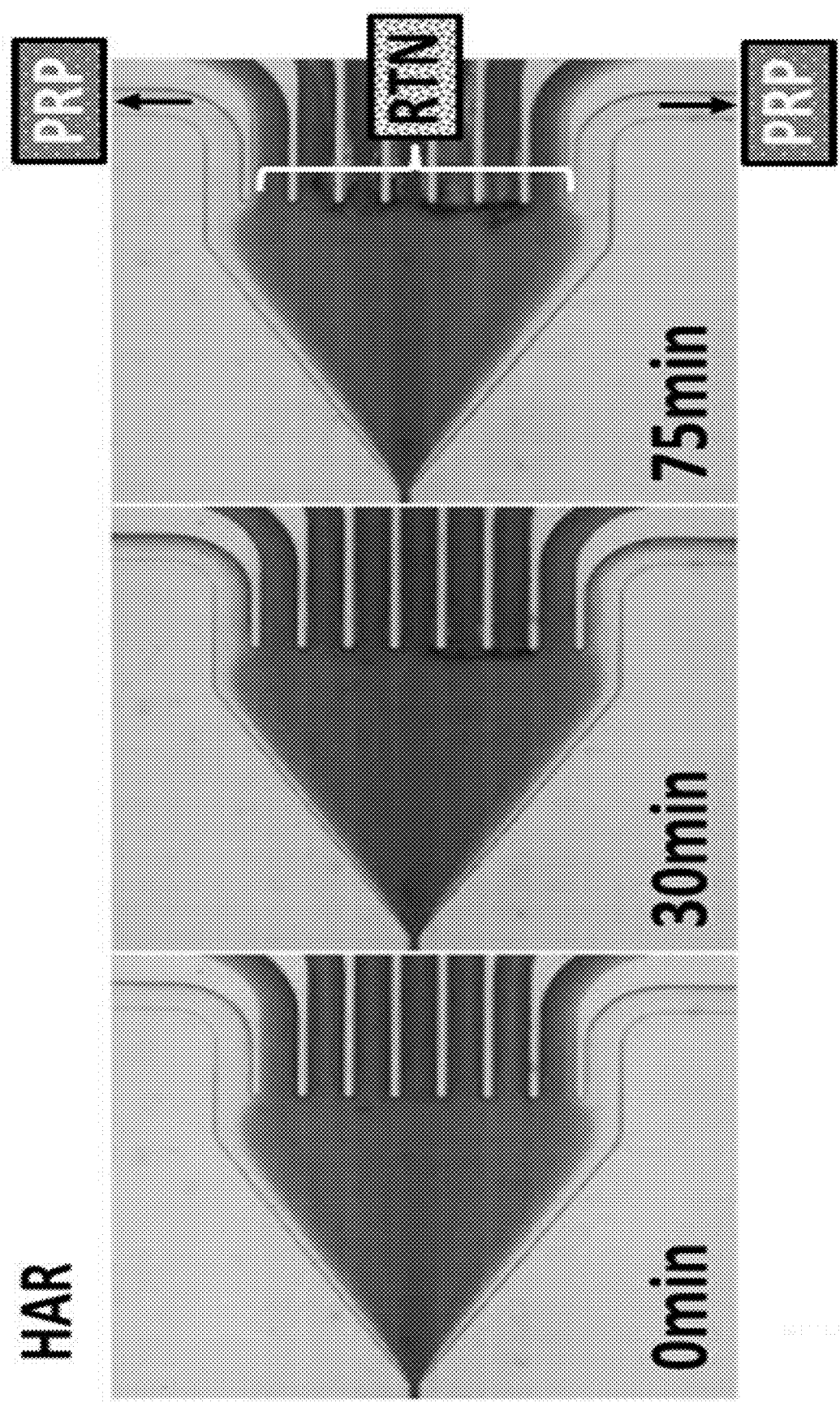
FIG. 5A shows the inertial focusing of RBCs and WBCs in the expansion channel close to the outlet.

In the example shown in FIG. 5A, the flow trajectory of inertial focusing is shown in the expansion channel under bright field imaging. PLT-depleted sample were collected from outlets O2 to O8 as "Return". RBC-depleted and PLT-enriched PRP samples are collected in outlets O1 and O9 "PRP" outlets. On average, about 4 mL of WB was processed with single set of microfluidic devices in single pass without clogging at processing time of about 1 hour.

Figure 5B:
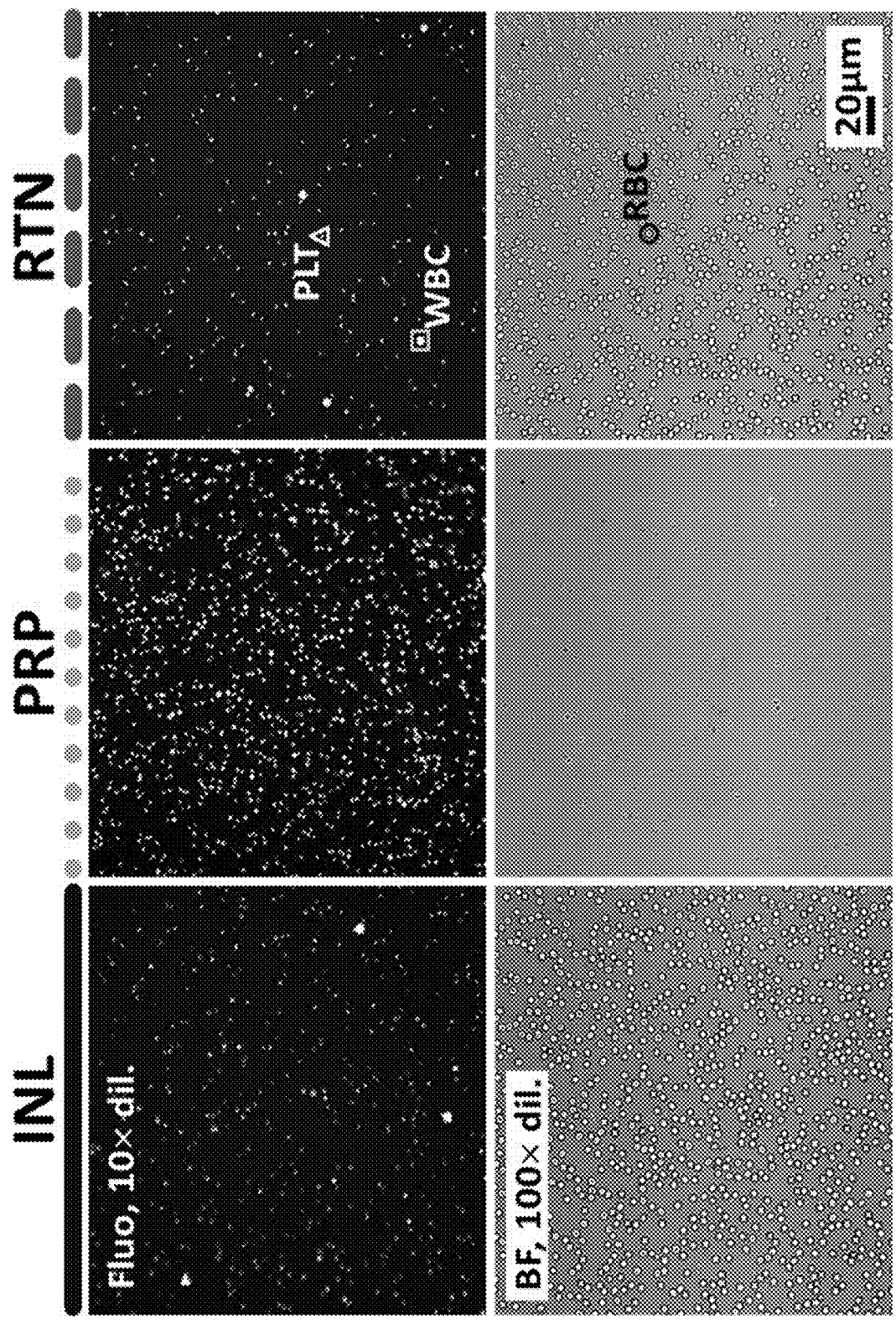
FIG. 5B shows the cell count (Square: WBC; Triangle: PLT, and Circle: RBC) counting under cell counting chamber.
Figures 5C, 5D:
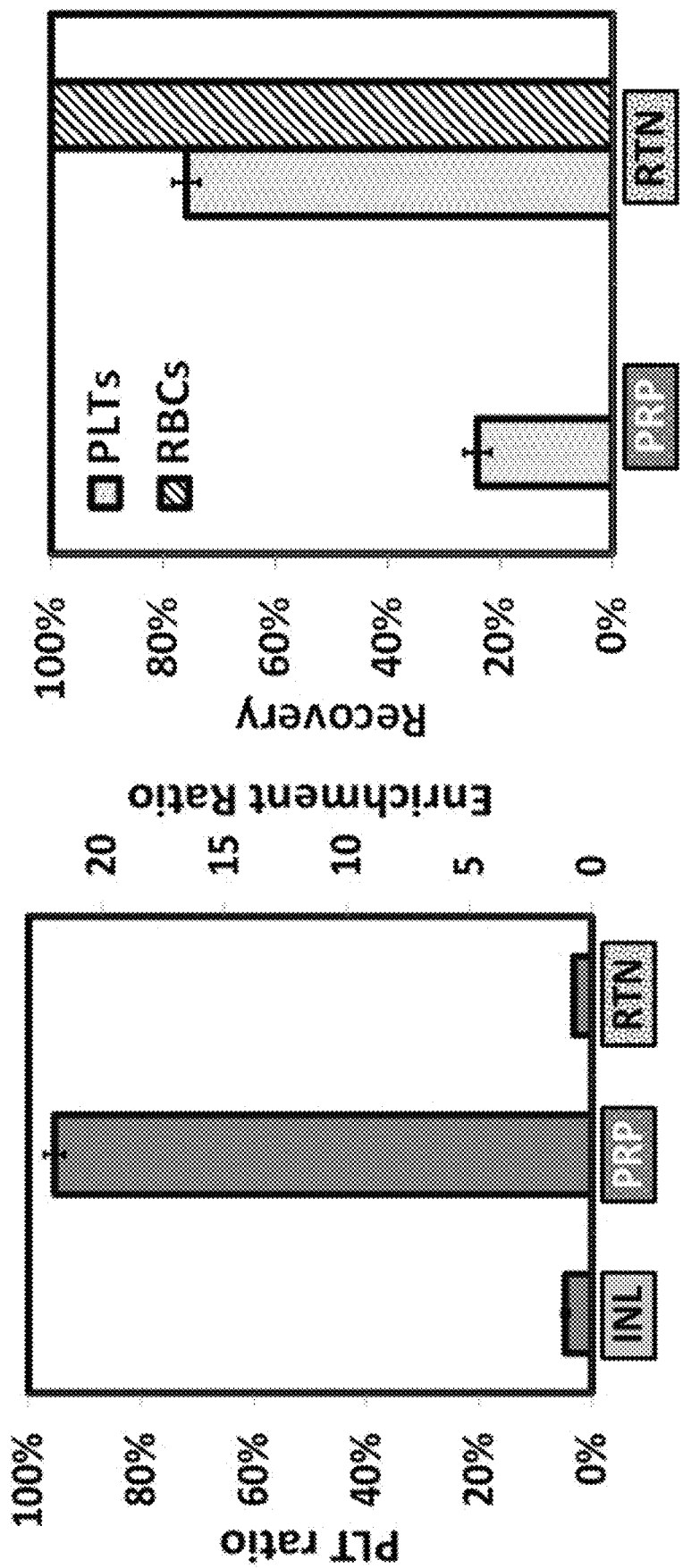
FIG. 5C shows the PLT ratio and enrichment plots (INL is inlet, PRP is platelet rich portion, RTN is return to patient).
FIG. 5D shows the recovery plot (PRP is platelet rich portion, RTN is return to patient).

FIGS. 5A-5D demonstrate WB sorting with the HAR rectangular straight microfluidic channel assembly at volume flow rate of Q=80 μL/min with undiluted WB: FIG. 5A shows the inertial focusing of RBCs and WBCs in the expansion channel closed to the outlet; FIG. 5B shows the cell count (Square: WBC; Triangle: PLT, and Circle: RBC) counting under cell counting chamber; FIG. 5C shows the PLT ratio and enrichment plots; and FIG. 5D shows the recovery plot.

The purity, recovery and enrichment ratio were determined as the follows:

$$\text{Purity}[PLT] = \frac{[C_{PLT}]}{[C_{PLT}] + [C_{RBC}] + [C_{WBC}]} \quad [1]$$

$$\text{Recov}[RBC]_{Return} = \frac{[N_{RBC}]_{Return}}{[N_{RBC}]_{PRP} + [N_{RBC}]_{Return}} \quad [2\text{-a}]$$

$$\text{Recov}[PLT]_{PRP} = \frac{[N_{PLT}]_{PRP}}{[N_{PLT}]_{PRP} + [N_{PLT}]_{Return}} \quad [2\text{-b}]$$

$$\text{Enrich}[PLT]_{PRP} = \frac{\text{Purity}[C_{PLT}]_{PRP}}{\text{Purity}[C_{PLT}]_{Inlet}} \quad [3]$$

where [$N_{PLT}$], [$N_{RBC}$] & [$N_{WBC}$] are the number of PLTs, RBCs and WBCs collected from the inlet or outlets, while [$C_{PLT}$], [$C_{RBC}$] & [$C_{WBC}$] are the concentration of PLTs, RBCs and WBCs from the inlet or outlets respectively.

The cell samples collected from inlet, outlet "PRP" and "Return" were counted with bright field and fluorescence imaging in FIG. 5B. The RBCs (circle) portion of all samples was counted in bright field imaging with 100× dilution in 10% ACD 1×PBS. The WBCs and PLTs portion were counted with 10× dilution and Calcein AM staining in fluorescence images. Cells with >4 μm diameter were counted as WBCs (square), while cells with diameter <4 μm were counted as PLTs (triangle). The sorting performance was summarized in FIGS. 5C and 5D. For single pass operation, the microfluidic module recovered 99.95% of RBCs. The PLT ratio in the "PRP" collection was 95.4%, which is enriched 21.6× from an initial PLT ratio of 4.7%. On average 24.1% of PLTs were extracted in the "PRP" collection. WBC concentration is reduced ~7× in the outlet "PRP" compared to the inlet. On average, less than 0.05% of RBCs were collected in the outlet "PRP".

PLT Concentrator Unit

In some embodiments, the focusing region of the PLT concentrator unit can include a straight high aspect ratio (HAR) channel (e.g., height>width) that has more height than width. For example, the PRP sample collected from the WB sorter is injected to the PLT concentrator. The PLTs forms two focused trajectories as they traverse the HAR focusing channel into the expansion outlet channel of the PLT concentrator, the PLT focusing streams are somewhat towards the two side walls or generally away from the true center with plasma substantially devoid of PLTs adjacent to the side walls. The PLT concentrator has two focused PLT streams that are not along the walls, and thereby the function of the PLT concentrator is different from the WB sorter. Even the regions more centrally to the PLT focusing streams have less PLT than the focusing streams, but more PLT than the outer side wall streams of plasma. The PLT content of the PRP sample can be concentrated and collected in the side channel outlets of the concentrator due to the PLT trajectory, which can be formed into and extend from the sides, top, or bottom of the main channel, or from respective side channels when circular or elliptical cross-sectional profile. The PLT concentrator can be configured similarly to the WB sorter, and located downstream from the WB sorter. That is, FIG. 2A can represent the structure of the PLT concentrator. The difference is the outlet in the concentrator that receive the concentrated platelet fraction is not the outer channels or side channels, but the concentrated platelet fraction are the channels inward or medial or downstream from the outer channels or side channels. In the concentrator, the side channels (e.g., ultimate from central axis) are for a platelet poor plasma (PPP) portion. The next inward channels (e.g., penultimate from central axis) collect the platelet concentrate. Then, the next inward channels (e.g., medial to antepenultimate) collect platelets but at lower concentration than the platelet concentrate.

In some embodiments, a leukocyte reduction filtering unit can be included in the microfluidic system downstream or after the PLT concentrator unit to decrease the WBC concentration in the "PC". The leukocyte reduction filtering unit can be downstream from the opening of the side channels.

In the concentrator, the main channel or other side channels downstream from the openings of the side channels can be used to collect the other portion of the "PRP" sample. The concentrator side channels are used as "PPP" (platelet-poor plasma) outlets and then routed to return to the blood donor to prevent excess loss of plasma.

In an embodiment of a PLT concentrator unit, the fluorescently labeled human PLTs are used to characterize the performance of HAR microfluidic channel device (FIG. 6A) for PLT concentrating. As shown, the expansion region is not an inverse taper, but a full expansion into a larger conduit. Although a full 90-degree expansion channel is shown, other expansion geometries work as well.

Figure 6A:
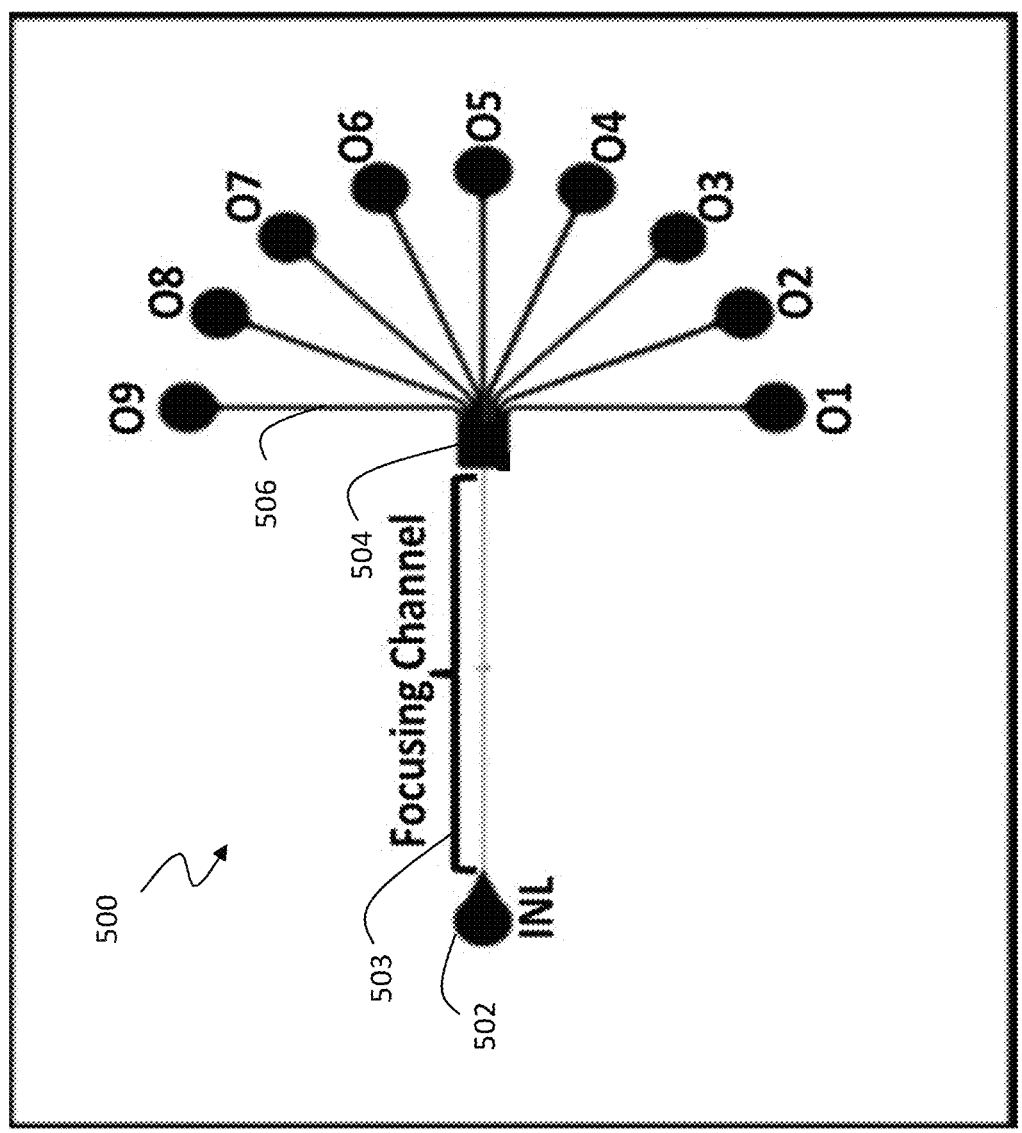
FIG. 6A shows the PLT concentrator includes the inlet (INL) that feeds a focusing channel into a separator region (e.g., outlet expansion channel) that has the arranged outlet lines that correspond with outlets O1 through O9.

FIG. 6A shows the PLT concentrator 500 includes the inlet 502 (INL) that feeds a focusing channel 503 into a separator region 504 (e.g., outlet expansion channel) that has the arranged outlet lines 506 that correspond with outlets O1 through O9 (as defined herein). The outlet lines 506 of O1 and O9 outlets can go to reservoirs or be used to collect the contents of each output line, or they can be used as input into a next stage, or appropriately recycled back.

Figure 6B:
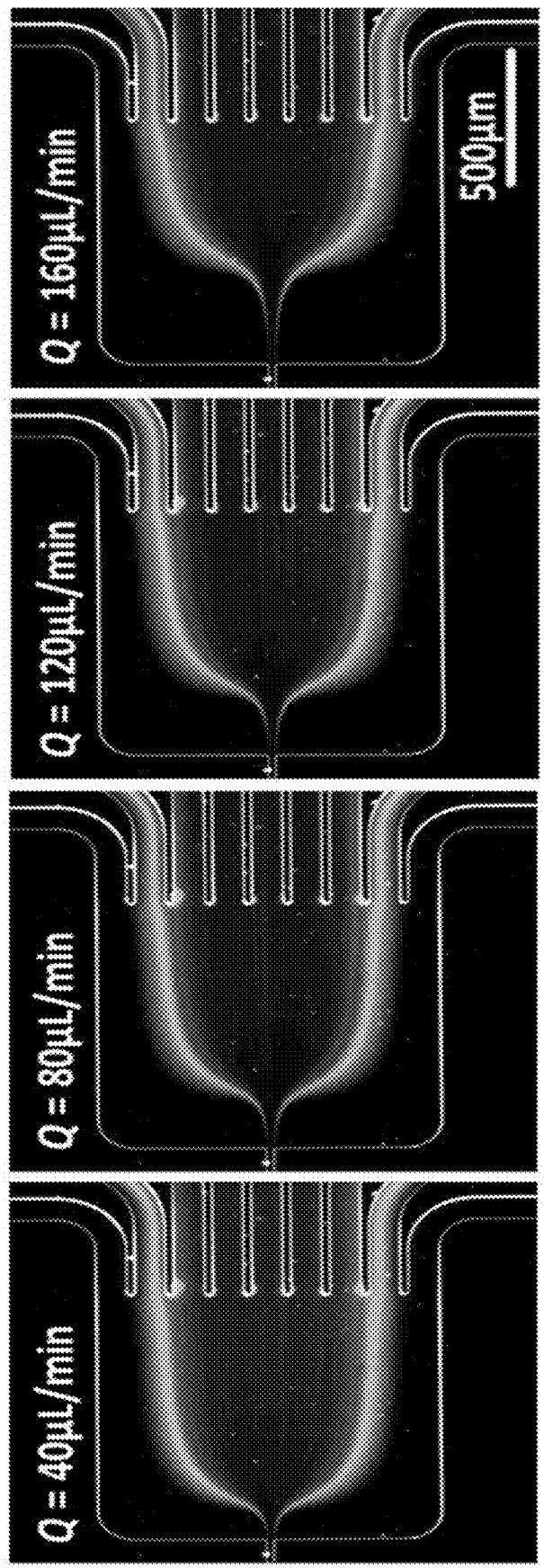
FIG. 6B shows the focusing and collection of Calcein AM stained human PLTs in the expansion channel at different flow rates 40-160 μL/min.
Figure 6C:
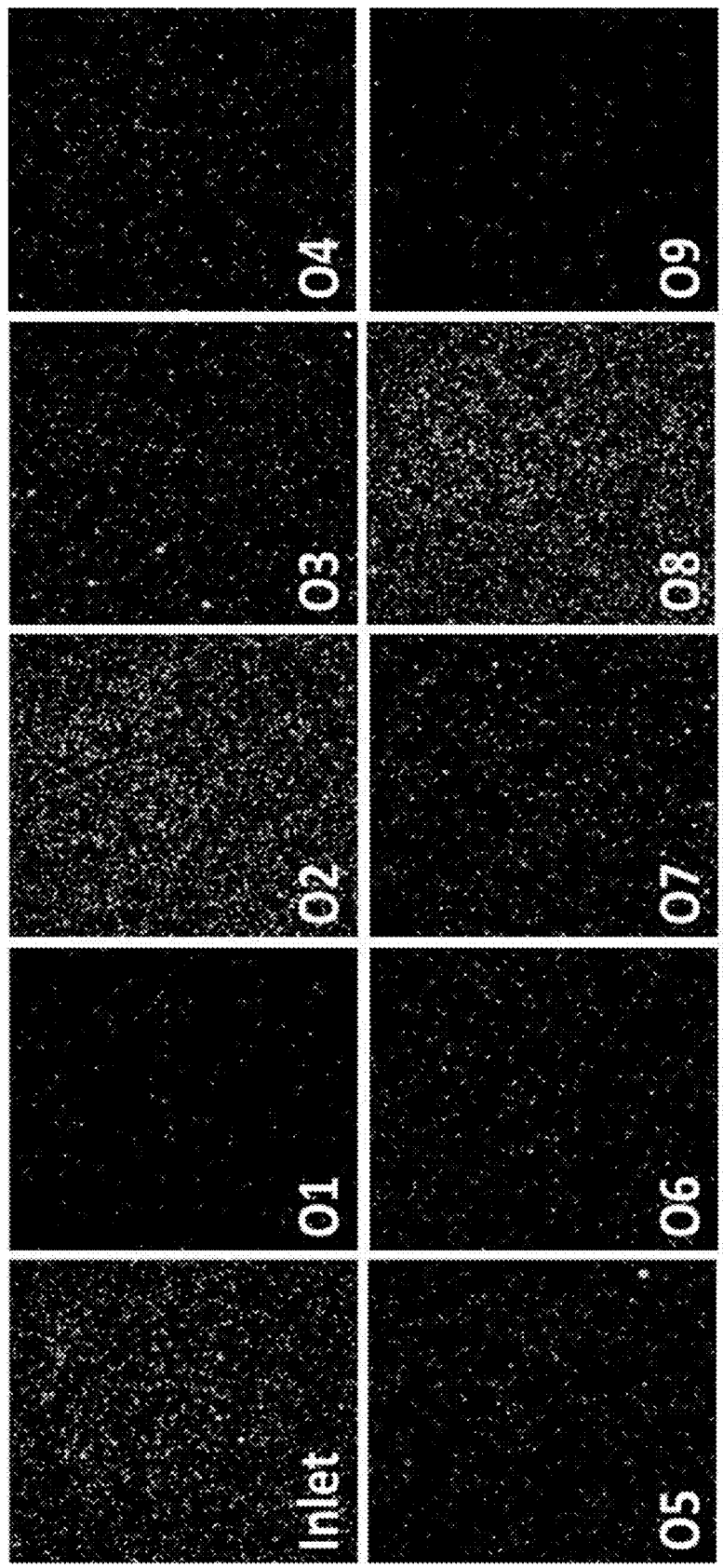
FIG. 6C shows the collection enriched/depleted human PLTs at different outlets at average flow rate of 120 μL/min.

The expansion point of the PLT concentrator unit is shown in FIG. 6B, which demonstrates the inertial focusing of Calcein AM stained PLTs in the sudden expansion channel (e.g., no expansion inverse taper) at flow rate ranged from 40 μL/min to 160 μL/min. Two PLT focused flow trajectories were formed near the side walls of the expansion channel. Most fluorescently labeled PLTs were directed to collection outlets O2 and O8 (e.g., platelet concentrate). Still, a good portion of platelets was collected from outlets O3 to O7. Very few PLTs flowed into outlets O1 and O9 (platelet poor plasma). In FIG. 6C, concentrated/filtrated Calcein AM stained PRP samples collected from outlets O1 to O9 were counted. The average volume flow rate was Q=120 μL/min. Accordingly, the plasma that is poor in platelets (PPP) can be collected from outlets O1 and O9.

FIGS. 6A-6C show the concentration of PRP with the high AR straight rectangular microfluidic channel device (e.g., sudden expansion or sharp expansion without an inverse taper): FIG. 6A shows the device layout with focusing channel of 8 mm length, 20 μm width and 50 μm height, and 9 outlets; FIG. 6B shows the focusing and collection of Calcein AM stained human PLTs in the expansion channel at different flow rates 40-160 μL/min; and FIG. 6C shows the collection enriched/depleted human PLTs at different outlets at average flow rate of 120 μL/min. About 65% of PLTs were collected in outlets O2 and O8, resulting in PLT concentration factor of 3×. 96% PLTs were retained from outlets O2 through O8 with only 4% PLT lost in outlets O1 and O9. In this case, a concentration factor of 1.3× is resulted.

Schematic of the Connection of Serial WB Sorter and PLT Concentrator Units

Figure 7A:
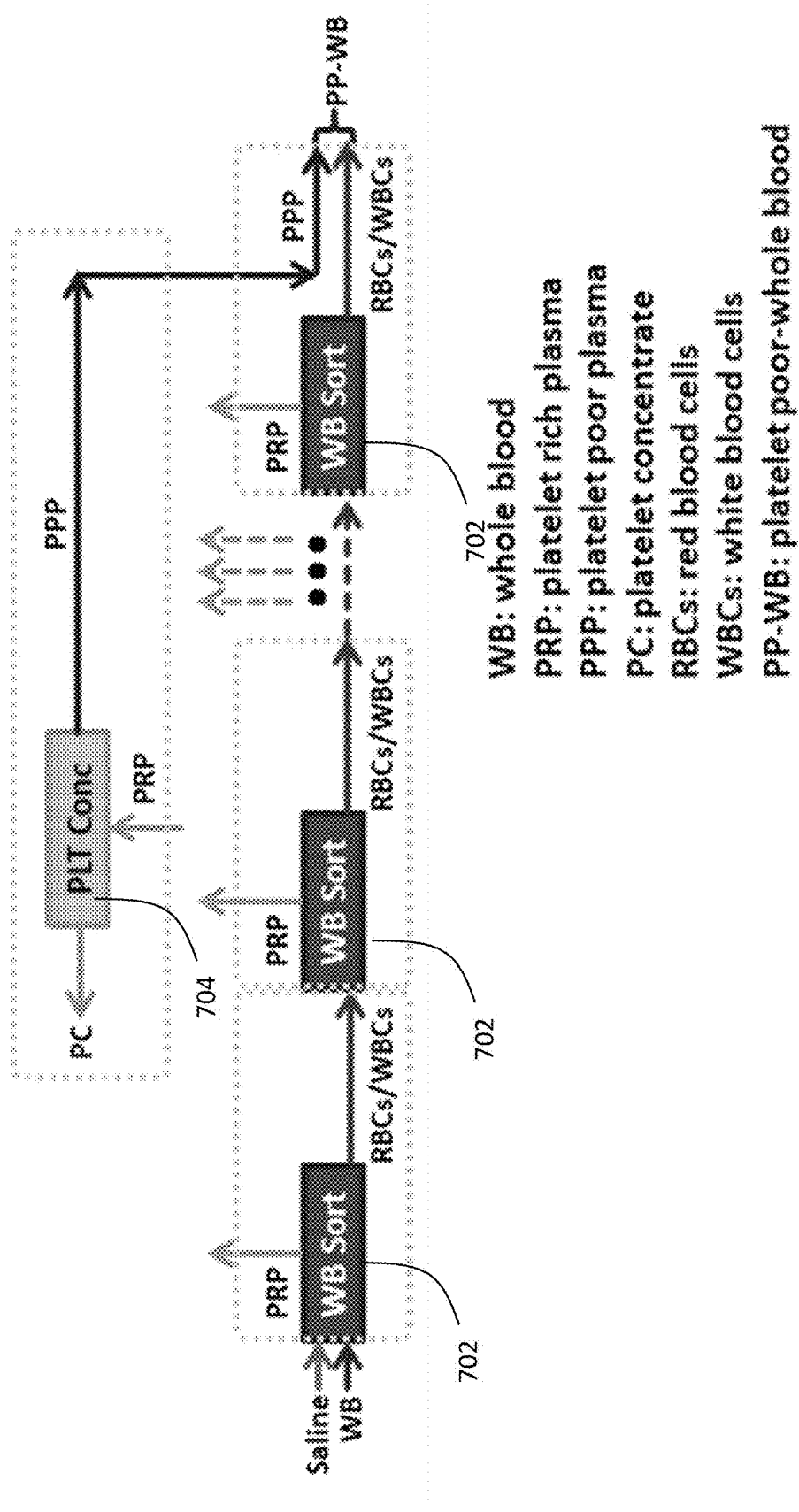
FIG. 7A shows Scheme I, where the PRP extracted from all whole blood sorter units is collected and processed with one common PLT concentrator unit.
Figure 7B:
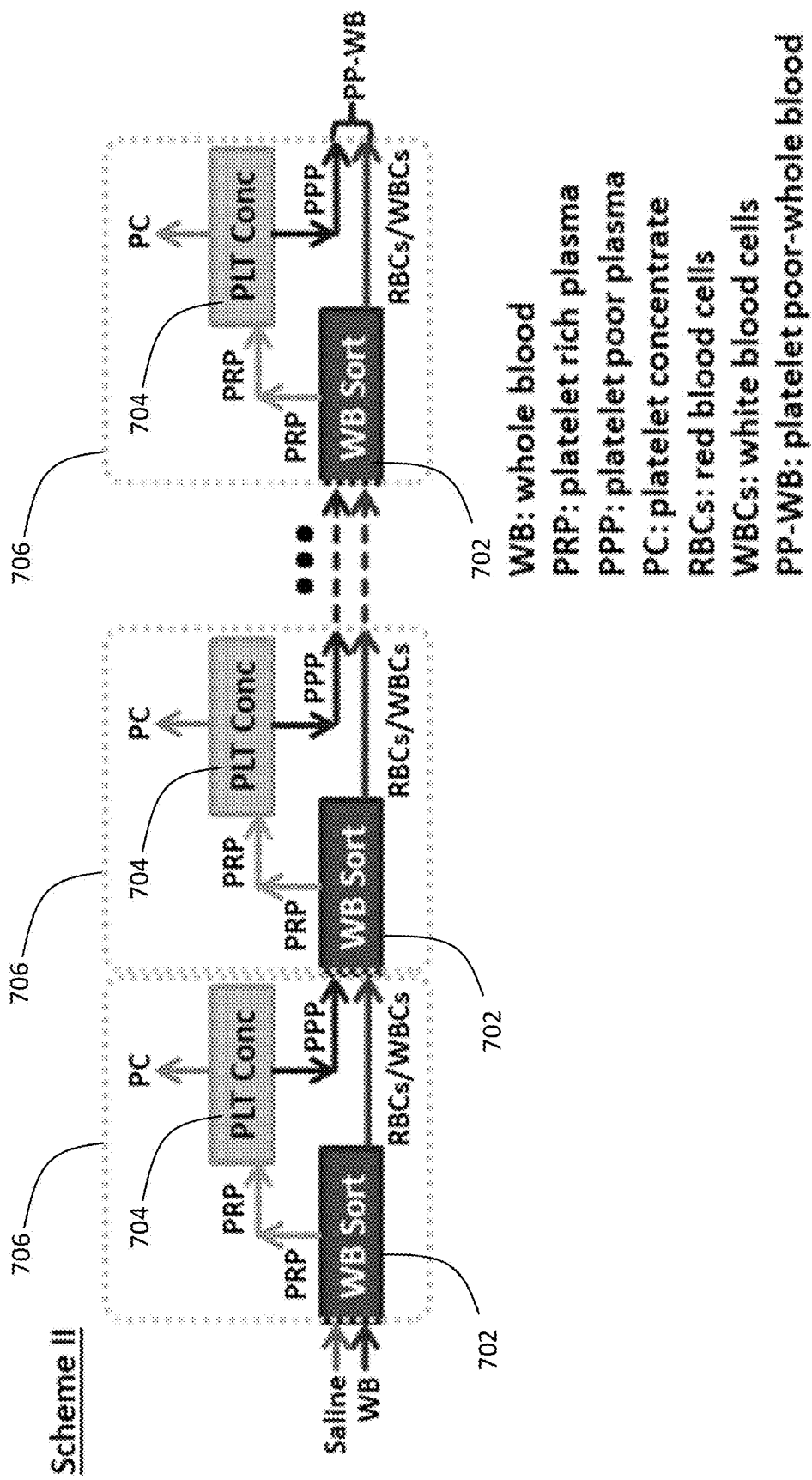
FIG. 7B shows Scheme II, where each PLT extraction unit consists of a pair of a whole blood sorter and a PLT concentrator, where the PPP is re-injected to the next unit to improve PLT recovery and extraction efficiency.

The microfluidic module with optimized outlet recovery has good sorting performance with high PLT purity in outlet "PRP" and high RBCs recovery in outlet "Return". However, the single pass PLT extraction efficiency is low (~25%). Higher platelet extraction efficiencies can be achieved by connecting multiple high aspect ratio (HAR) sorters in a serial manner We identified two different schemes for collecting the HAR sorters along with platelet concentrators (PLT Conc) that will allow realization of the portable apheresis device capable of producing platelet product with desired quality (FIGS. 7A-7B). The schemes include Scheme I and Scheme II.

Scheme I: The PLTs will be continuously extracted from the serially arranged WB sorters. All PLTs extracted will be collected and concentrated using one common PLT concentrator. The advantage of this scheme is the ease of fabrication due to less fluidic interconnects. However, a single PLT concentrator will require the ability to extract platelets with a high PLT recovery efficiency. Scheme II: This arrangement requires more complicated fluidic interconnects. Each repeating unit is composed of a pair of WB sorter and PLT concentrator. Platelet concentrate (PC) will be extracted in each PLT concentrator and platelet poor plasma (PPP) will be routed to the WB sorter in the next unit. The addition of PPP to the next WB sorter will help in preventing excess loss of plasma. This approach imposes lower requirement on PLT recovery efficiency for the PLT concentrator and is expected to have higher overall recovery of PLT.

FIGS. 7A-7B show schematics of PLT apheresis device for undiluted continuous WB processing. WB sorter operates based on PLT margination effect. PLT concentrator operates based on inertial focusing of PLTs.

FIG. 7A shows Scheme I, where the PRP extracted from all WB Sorter units is collected and processed with one common PLT concentrator unit. As such, saline and whole blood (WB) are input into a whole blood sorter 702, where the platelet rich portion (PRP) is withdrawn and the RCB/WBC portion goes to a second whole blood sorter 702, which can be repeated to have "n" whole blood sorters, where n is an integer. The PRP from each WB sorter 702 is input into a platelet concentrator 704, which obtains the platelet poor plasma (PPP) and the platelet concentrate (PC).

FIG. 7B shows Scheme II, where each PLT extraction unit 706 consists of a pair of a WB sorter 702 and a PLT concentrator 704. The PPP is re-injected to the next unit (706) to improve PLT recovery and extraction efficiency.

Figure 8:
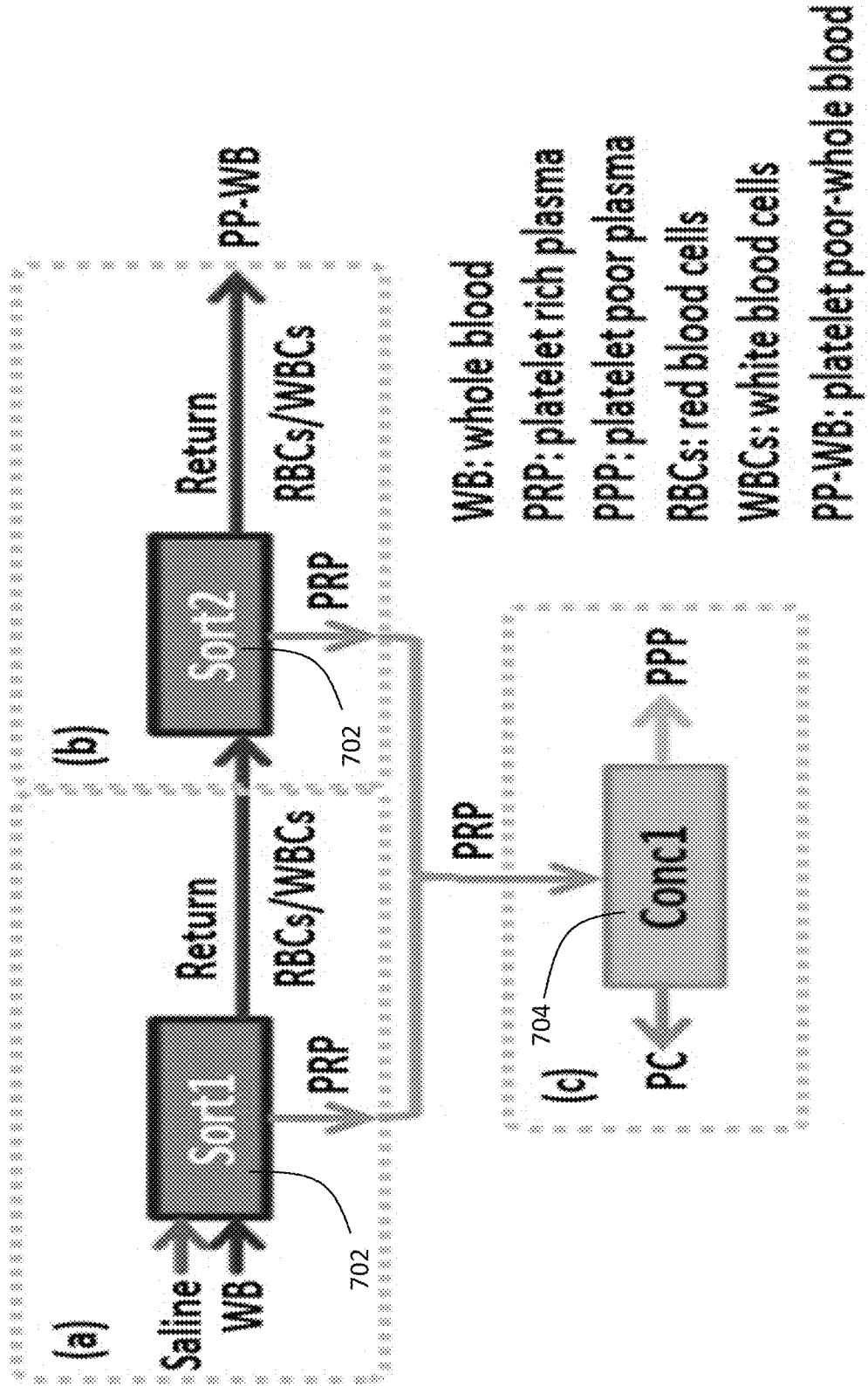
FIG. 8 shows an example of serial whole blood sorting, PLT extraction and concentration in batch processing mode: (a) $1^{st}$ PLT extraction from WB Sort1 (sorter); (b) $2^{nd}$ PLT extraction from WB Sort2 (sorter); and (c) PLT concentration from PLT Conc1 (concentrator) from both WB Sort1 and WB Sort2.

Scheme I was implemented using two WB sorters (Sort1, Sort2) and one PLT concentrator (Conc1) in batch processing operation using whole blood as input sample (FIG. 8).

FIG. 8 shows an example of serial WB sorting, PLT extraction and concentration in batch processing mode: (a) $1^{st}$ PLT extraction from WB Sort1 (702); (b) $2^{nd}$ PLT extraction from Sort2 (702); and (c) PLT concentration from PLT Conc1 (704) from both WB Sort1 and WB Sort2.

The operation parameters and experimental conditions of both Sort1 and Sort2 were similar to single pass experiment in the previous section. Both Sort1 and Sort2 feature identical microfluidic modules. The sample collected from outlet "Return" of Sort1 was re-injected to the inlet of Sort2. We found that the PLT extraction efficiency in the $2^{nd}$ pass was similar to $1^{st}$ pass, which was about 25%. The PRP collected from $1^{st}$ and $2^{nd}$ WB sorter had purity >95%. Over 50% of PLTs from WB were collected with the two sorters.

We used HAR straight microfluidic channel as Conc1. The sample collected from outlets of "PRP" of Sort1 and Sort2 were mixed together and re-injected to the inlet of Conc1. The PLT concentration was increased in 2× in the outlet "PC" of Conc1.

Figure 9:
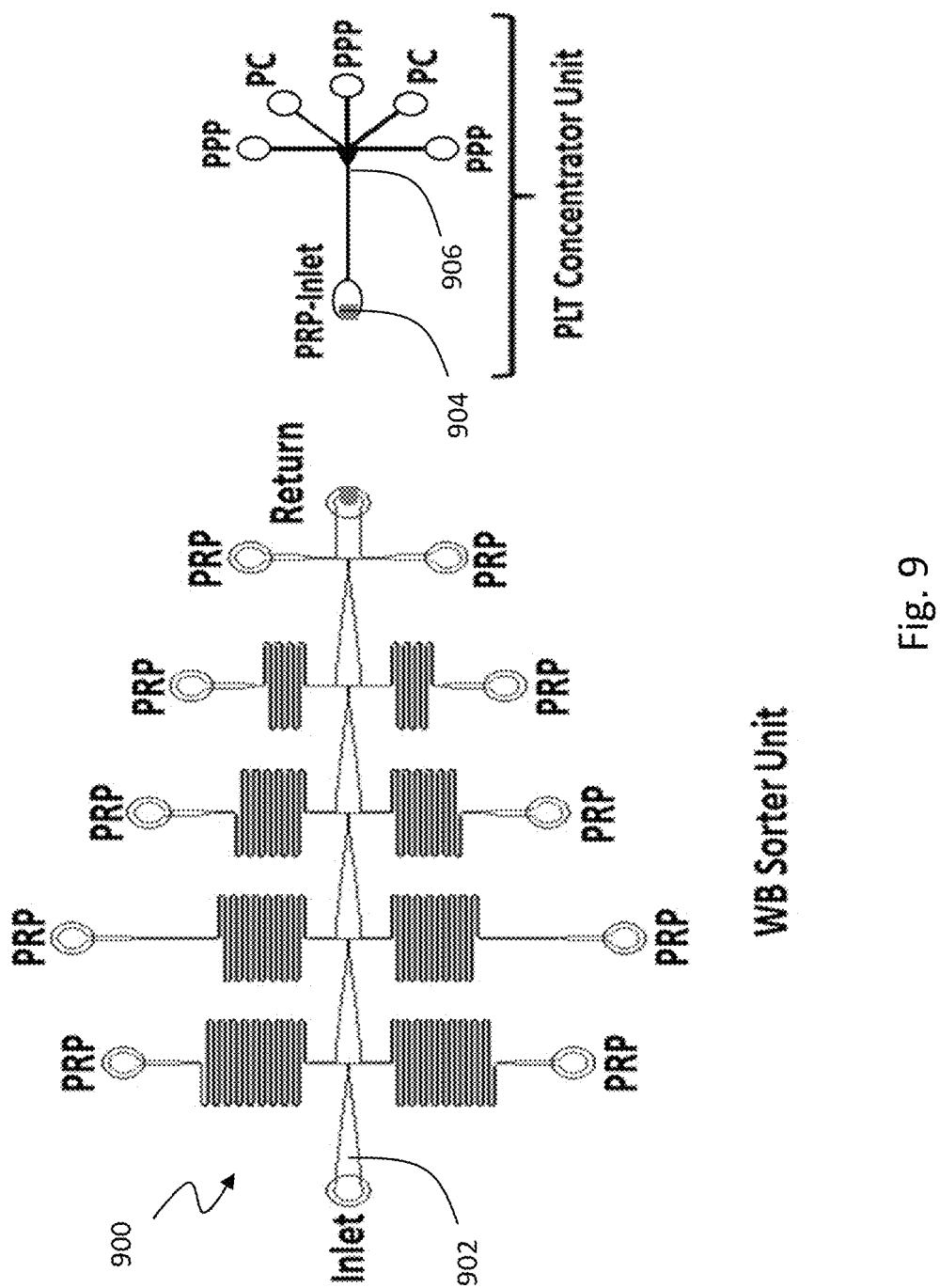
FIG. 9 shows a microfluidic design of Scheme 1 in continuous operation mode.

Microfluidic Design of Serial WB Sorters and PLT Concentrator Unit in Continuous Operation Mode Multiple WB sorter and PLT concentrator units are connected in serial configuration in continuous processing mode. An embodiment of the microfluidic design layout is illustrated in FIG. 9. Various outlets of both WB sorter and PLT concentrators are connected with fluidic resistance channels to optimize for sorting, concentration and recovery performance.

FIG. 9 shows a microfluidic design of Scheme 1 in continuous operation mode. The network 900 includes a sequence of stages, each having a WB sorter 902 that produces a plurality of plasma rich portions (PRP). The PRP are then connected (not shown) to the PRP inlet 904 of the PLT concentrator 906, which splits into the outer platelet poor plasma (PPP) portions and central platelet poor plasma (PPP) portions as well as the platelet concentrator (PC) outlets.

The total PLT extraction efficiency of serially connected WB sorters can be calculated as follow:

$$Extx[PLT]_{Sort}^{Total} = \sum_{i=1}^{N_{Sort}} Extx[PLT]_{Sort(i)} \quad [5]$$

$$Extx[PLT]_{Sort(i)} = Extx[PLT]_{Sort}^{Single} \times \left(1 - \sum_{i=1}^{N_{Sort}-1} Extx[PLT]_{Sort(i)}\right) \quad [6]$$

where $N_{Sort}$ is the number of WB sorters connected in serial configuration. $Extx[PLT]_{Sort}^{Single}$ is the single pass PLT extraction efficiency of the WB sorter. $Extx[PLT]_{Sort(i)}$ is the PLT extraction efficiency of individual WB sorter unit. According to equations [5], [6], the total PLT extraction efficiency with respect to the number of WB sorters connected in series is plotted in FIG. 10. The equation prediction agrees with experimental data for one (previously characterized at 24%) and two WB sorter units (~43%). The estimated total extraction for four serially connected WB sorters is 67%.

Figure 10:
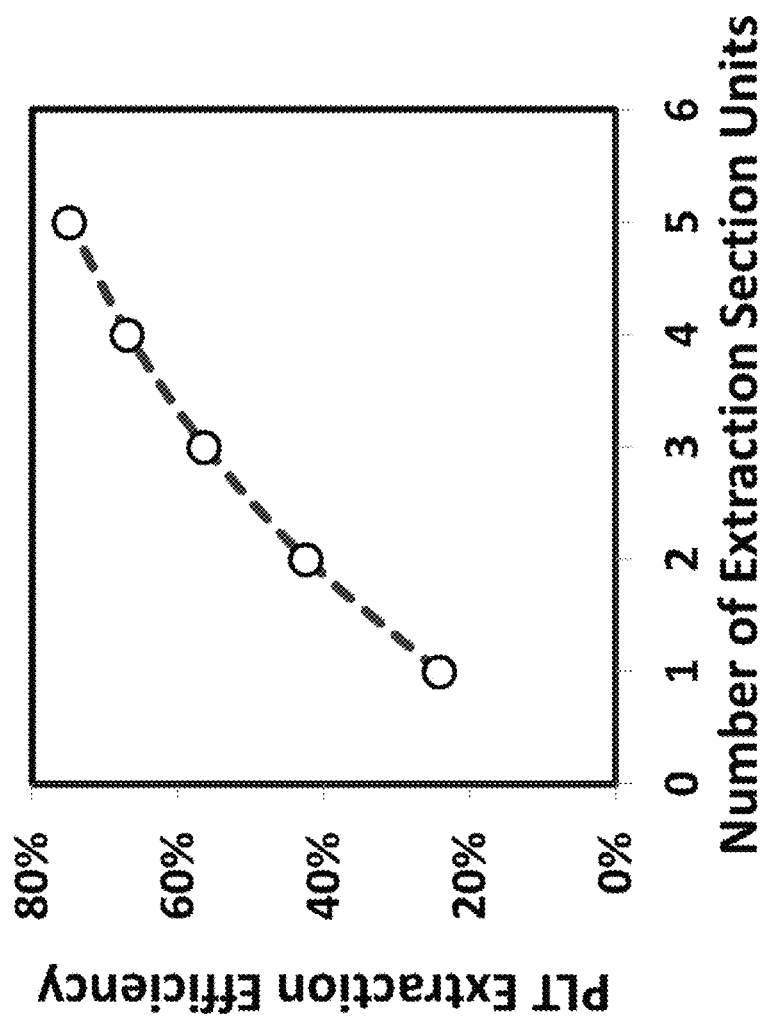
FIG. 10 plots the total PLT extraction efficiency with respect to the number of WB sorters connected in series.

FIG. 10 shows the PLT extraction efficiency with respect to the number of serial HAR microfluidic sorters. (broken line: theoretical prediction; circles: experimental data)

Microfluidic Design of Parallel Processing in Continuous Operation Mode

To scale-up throughput rate, multiple microfluidic WB sorter and PLT concentrator channels can connected in parallel (FIGS. 11A-11D). The outlets are grouped together to reduce structure complexity. The outlet channels were also designed to ensure fluidic resistance balance between "Collect" and "Discard" outlets for optimized sample recovery.

Figure 11A:
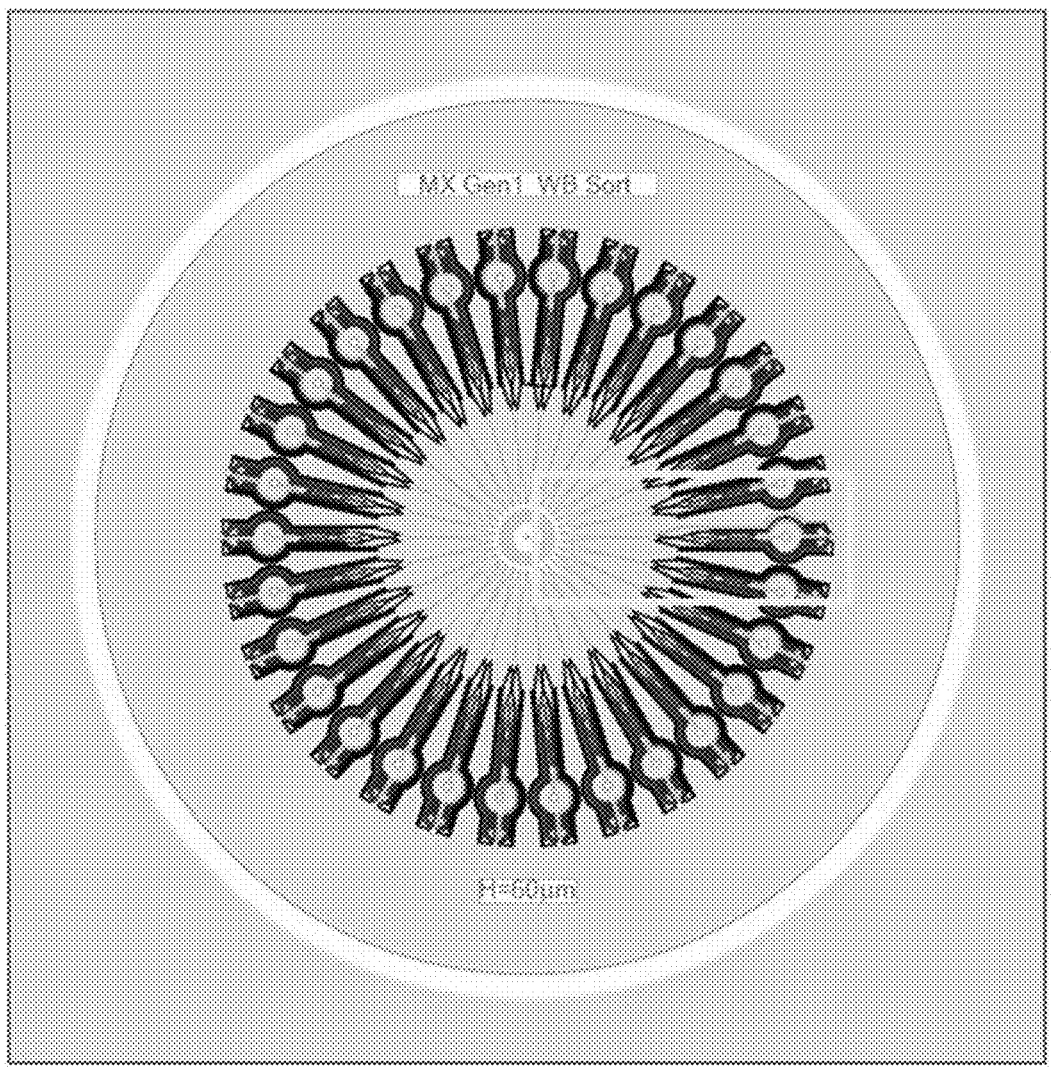
FIG. 11A shows a photomask layout of a platelet apheresis microfluidic plate.
Figure 11B:
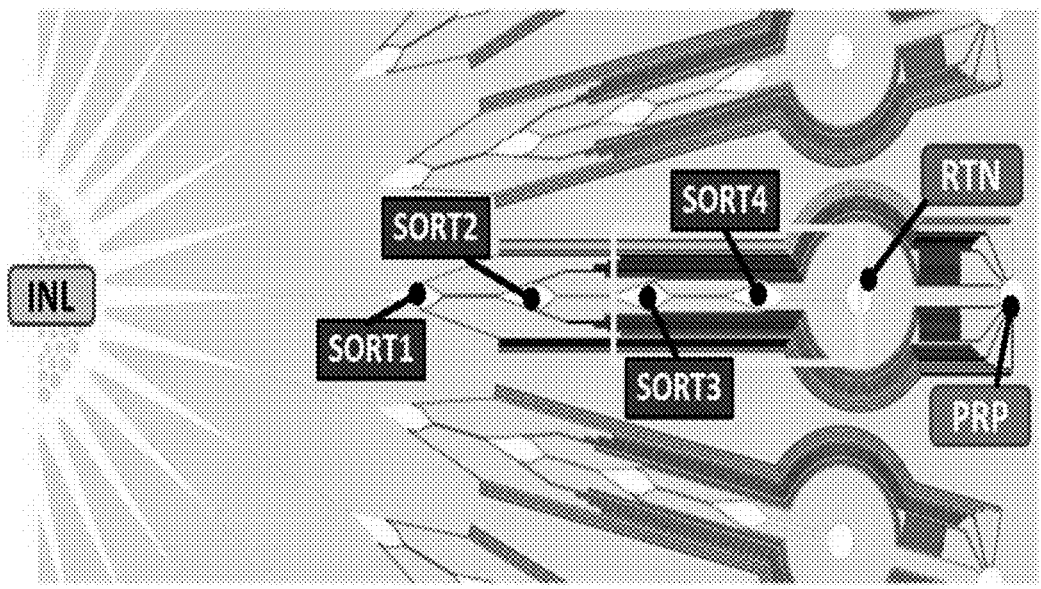
FIG. 11B shows that each branch containing four serially connected HAR WB sorters connected to a common inlet at the center.
Figure 11C:
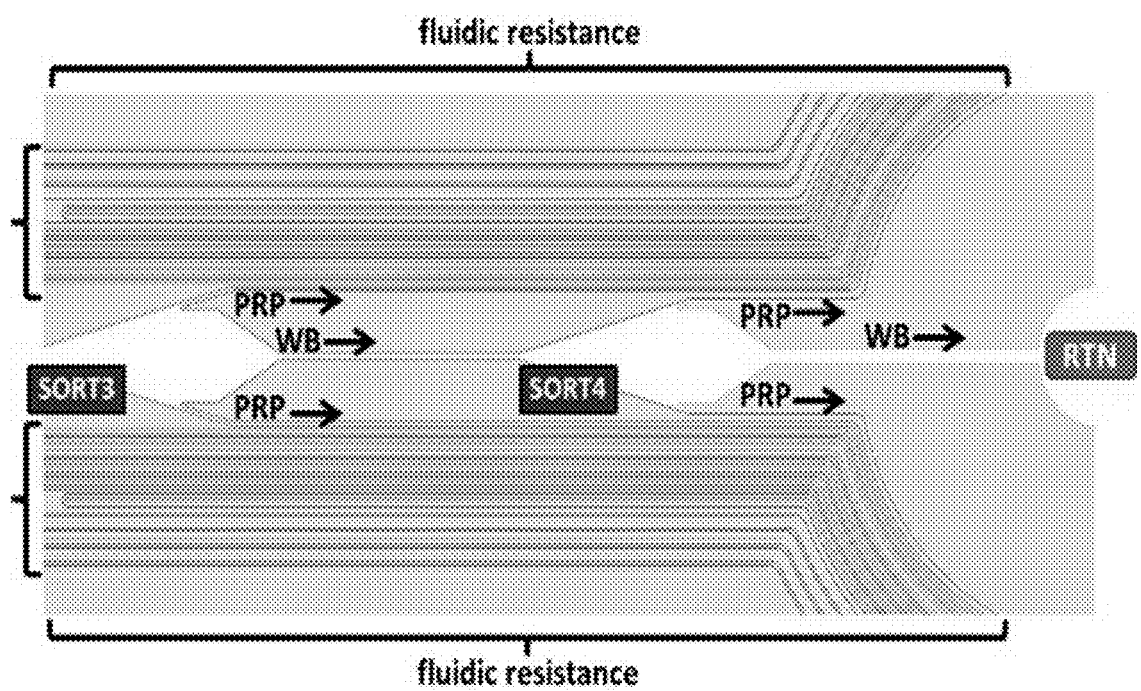
FIG. 11C shows that PLTs are collected by the "PRP" outlet on the side.
Figure 11D:
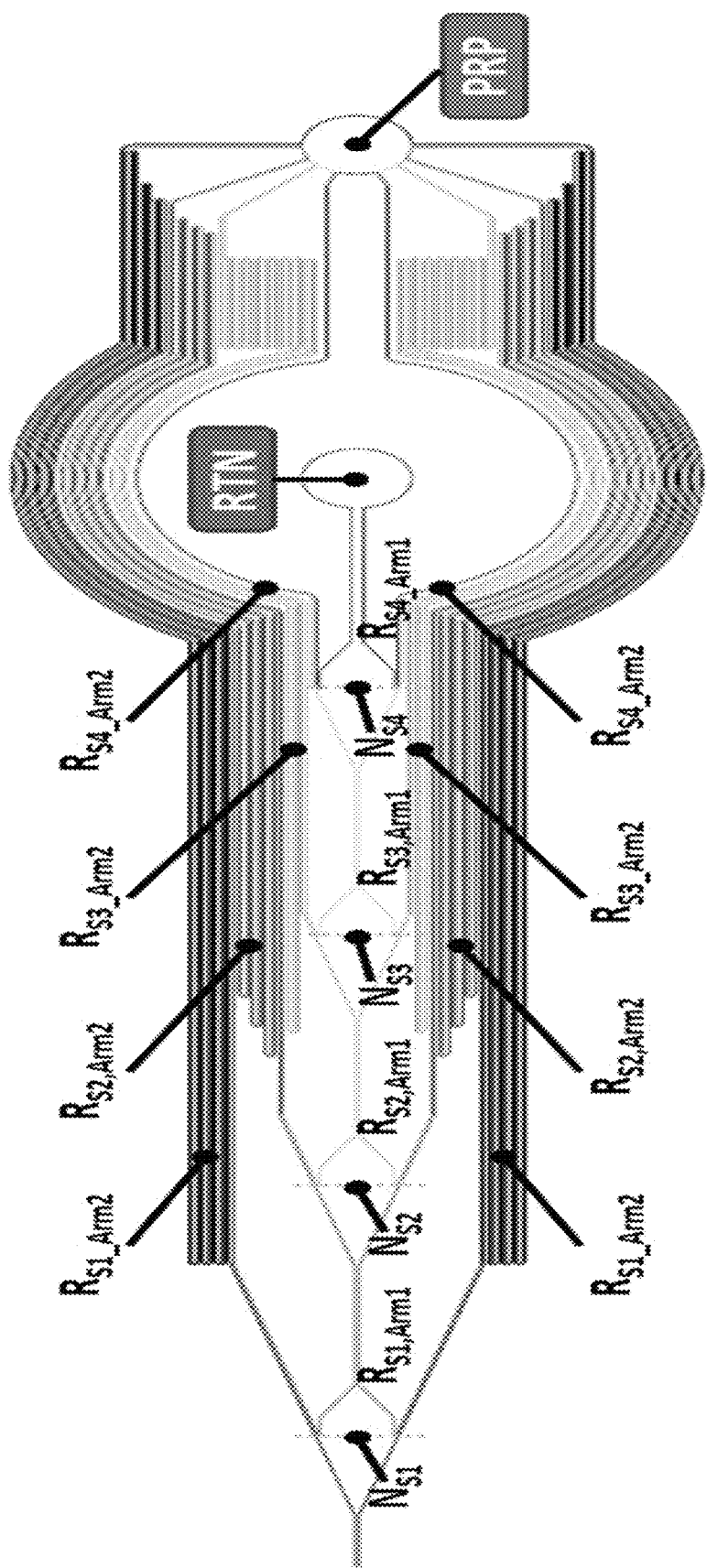
FIG. 11D shows that the "PRP/RTN" outlet volume ratio of each HAR sorter is designed to be 1:11 (the volume each "PRP" side outlet, Arm1 is 1:22 of the "RTN" outlet, Arm 2).

The photomask layout of an embodiment is shown in FIG. 11A. The platelet apheresis microfluidic plate contains 30 radially microfluidic branches. Each branch of the microfluidic plate resembles the design of its single-channel counterpart. Each branch containing four serially connected HAR WB sorters is connected to a common inlet at the center (FIG. 11B). The focusing channel of each HAR WB sorter has a cross section of 40 μm×60 μm (W×H). The RBCs experience high inertial force in the focusing channel and migrate to form a core along channel centerline. These abundant and deformable RBCs push smaller and rigid PLTs to marginate (e.g., distribute towards margins) towards the channel side walls. In each WB sorter, RBCs and WBCs are collected by the return ("RTN") outlet along the center-line in the expansion channel. PLTs are collected by the "PRP" outlet on the side (FIG. 11C). At each bifurcation node of each HAR WB sorter, the desired flow rate split is calculated and designed based on the fluidic resistance balance at each splitting arm. The "PRP/RTN" outlet volume ratio of each HAR sorter is designed to be 1:11 (the volume each "PRP" side outlet, Arm1 is 1:22 of the "RTN" outlet, as is Arm 2) as shown in FIG. 11D. The "PRP/RTN" outlet volume ratio was higher compared to 1:17.5 (each side outlet) in the previous single HAR WB sorter design as to ensure a higher single pass PLT extraction efficiency such that most PLTs can be extracted in the platelet apheresis microfluidic plate.

To reduce the complexity of fluidic circuitry, the "PRP" outlets of all WB sorters can be collected to a common outlet or their own for collection. Blood cells are returned to the donor. The platelet apheresis microfluidic prototypes were fabricated using PDMS soft lithography technique with SU-8 silicon mold. After casting with SU-8 mold, inlet/ outlet hole punching and oxygen plasma surface activation treatment, the PDMS piece containing the microfluidic features is bonded with a clean 4" glass plate. The assembled platelet apheresis microfluidic glass plate device was placed onto a 12 cm petri dish with inlet port encapsulated with another PDMS thick layer to sustain high pressure build-up near the inlet location for higher flow rate operation.

FIG. 11A-11D shows the photomask design for the WB Sort: FIG. 11A shows the overall layout; FIG. 11B shows a zoom-in of each branch; FIG. 11C shows a zoom-in of the fluidic resistance channel; and FIG. 11D outlet fluidic resistance calculation parameters.

Quality of PRP Products Subjected to Microfluidic Processing

Figure 12A:
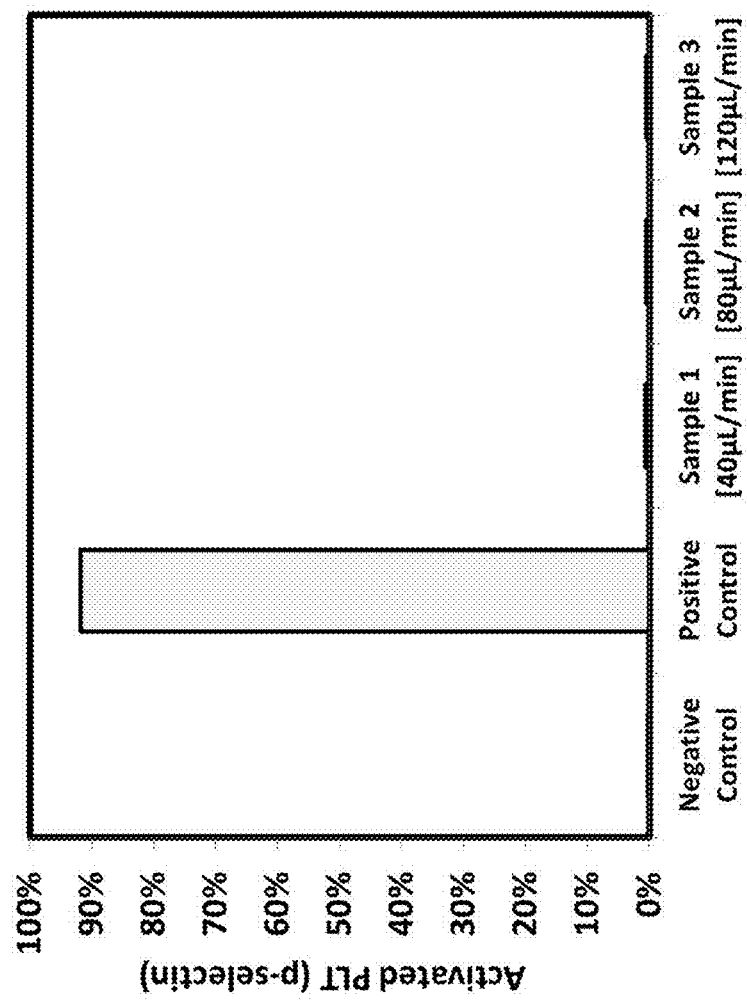
FIG. 12A includes flow cytometry data for PLT activation biomarkers.
Figure 12B:
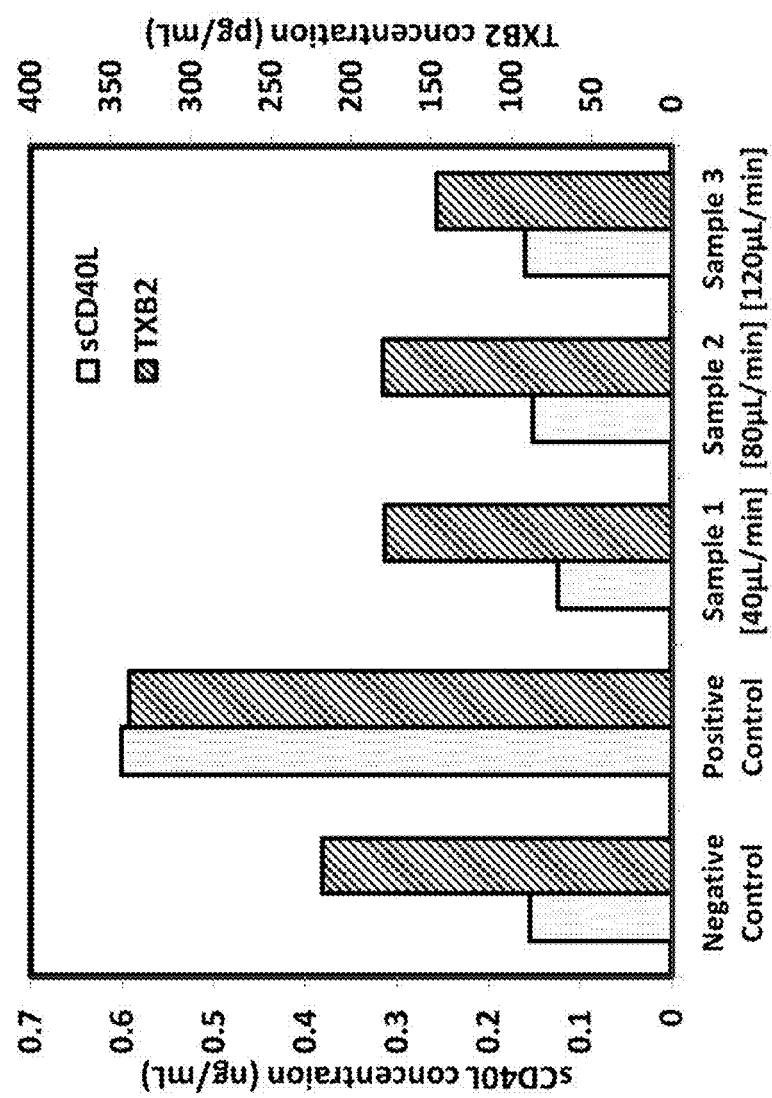
FIG. 12B includes ELISA data for PLT activation biomarkers.

We have showed that PLTs collected from the microfluidic processing maintained good morphology and remained un-activated. We tested the PLT activation status using PLT activation biomarkers both in flow cytometry and ELISA (FIGS. 12A-12B). PRP samples were prepared by centrifugation of WB at 1000×g for 10 minutes and collecting the supernatant. PLTs were collected by processing the PRP samples at flow rates ranging from 40 μL/min to 120 μL/min using the microfluidic sorter devices. Unprocessed PRP aliquot served as the negative control. Positive control was prepared by incubating unprocessed PRP aliquot in 100 nM Phorbol-myristate-acetate (PMA) for 30 minutes at 37° C. to induce platelet activation of CD62 antigen. For flow-cytometry measurements, samples were fixed in 0.5% formaldehyde immediately after sample preparation. Fixed PRP samples were labeled with fluorescently-conjugated anti-CD62P antibody and analyzed using a flow cytometer. Under proper gating and compensation threshold setting, positive control activated by PMA showed greater than 90% PLT activation, while negative control prepared by centrifugation and microfluidic processed samples showed negligible PLT activation, <0.5% (FIG. 12A). Commercial ELISA kits (Human sCD40L, BMS239 from ThermoFisher & Thromboxane B2, ab133022 from Abcam) were used for ELISA assays. Both PLT activation markers (sCD40L & TXB2) showed similar or less measurement level on microfluidic processed samples at all testing flow rates compared with both negative control (centrifugation processed) and positive control (activated by PMA) (FIG. 12B). The low PLT activation level from microfluidic processing can be attributed to the very short time exposure to high shear stress in the small microfluidic focusing channel, which is typically in the order of 10's of milli-second.

Multi-Layer Microfluidic Cartridges

Figure 14A:
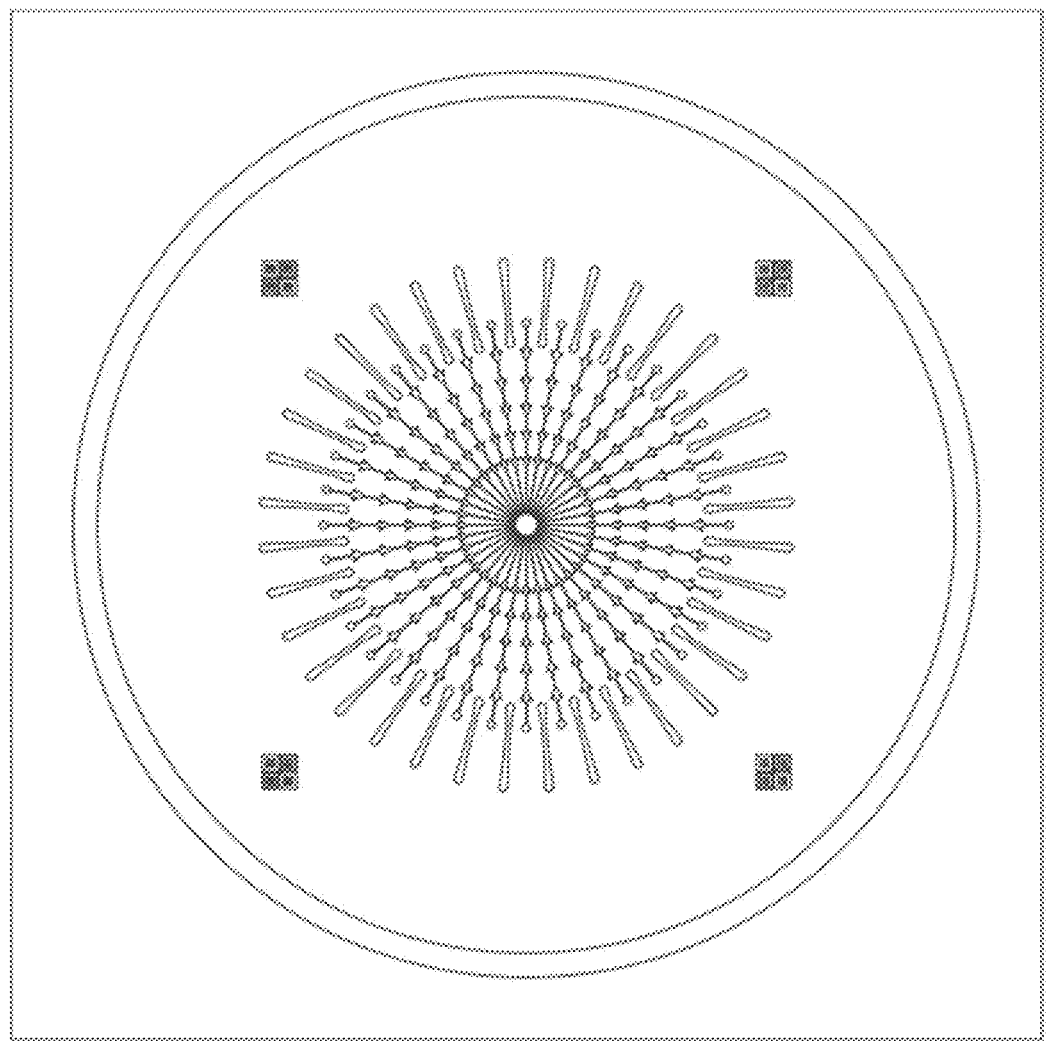
FIG. 14A shows the mask for the tall central channel region containing multiple sections of the constricting channel followed by expansion regions.
Figure 14B:
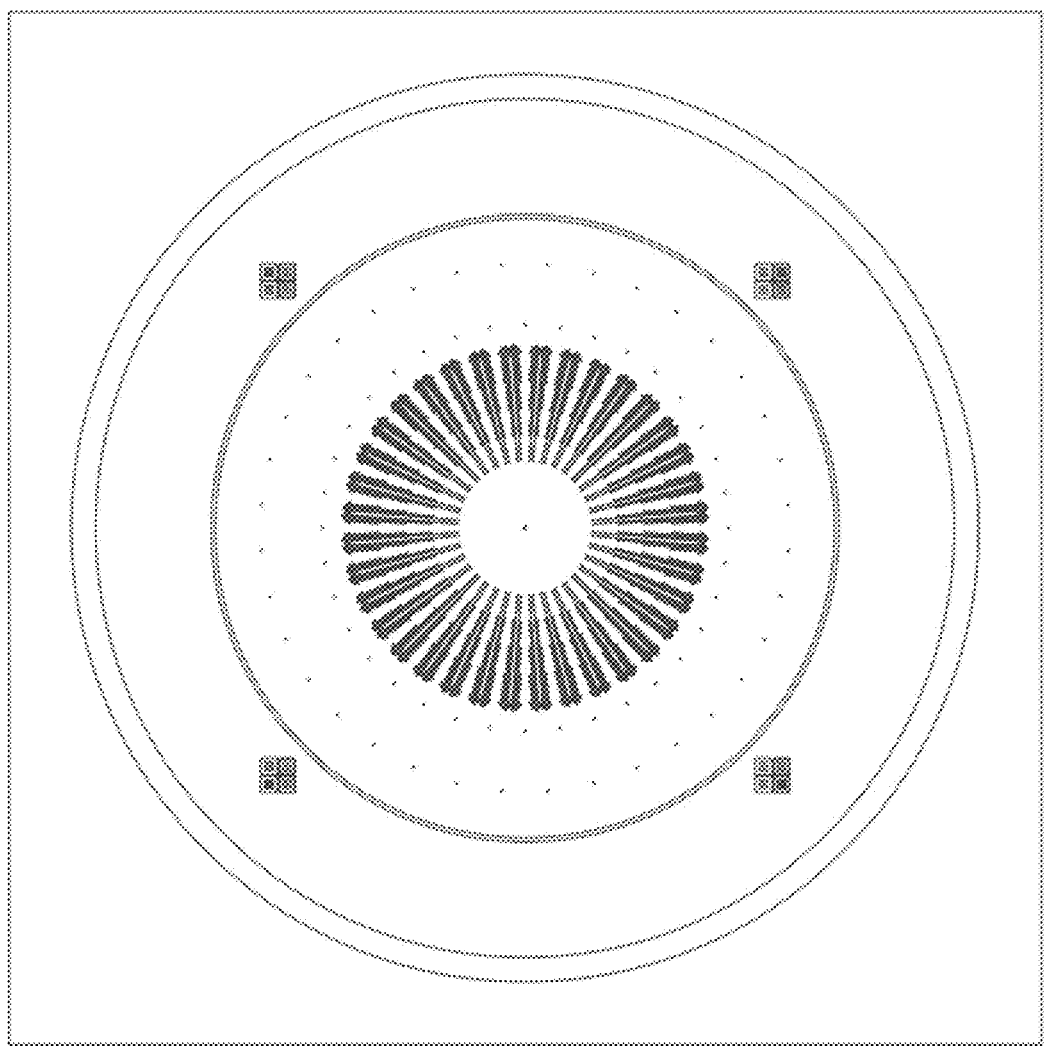
FIG. 14B is the mask layer for the shallow side extraction channels that add fluidic resistance to the platelet extraction arms.
Figure 14C:
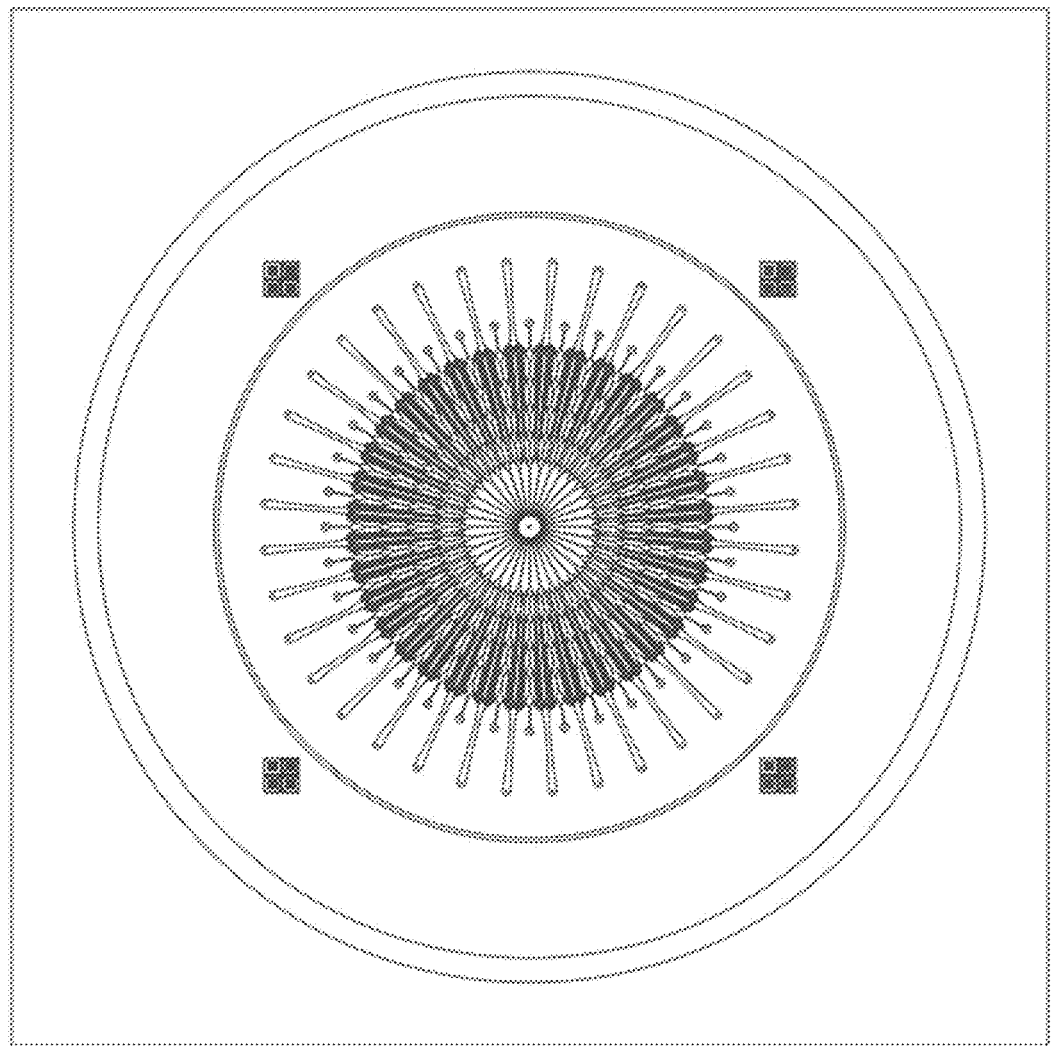
FIG. 14C is the overlay of the two layers of FIG. 14A and FIG. 14B.

Photomasks for another embodiment of the microfluidic cartridges is a design consisting of two different fluidic heights as shown in FIGS. 14A, 14B, and 14C. The microfluidic platelet extraction cartridge contains 36 radially arranged branches connecting in parallel to a single common inlet at the center. However, other numbers of branches may be used.

FIGS. 14A-14C shows the photomask designs for two-layer microfluidic cartridge. FIG. 14A shows the mask for the tall central channel region containing multiple sections of the constricting channel followed by expansion regions. FIG. 14B is the mask layer for the shallow side extraction channels that add fluidic resistance to the platelet extraction arms. FIG. 14C is the overlay of the two layers.

Figure 15A:
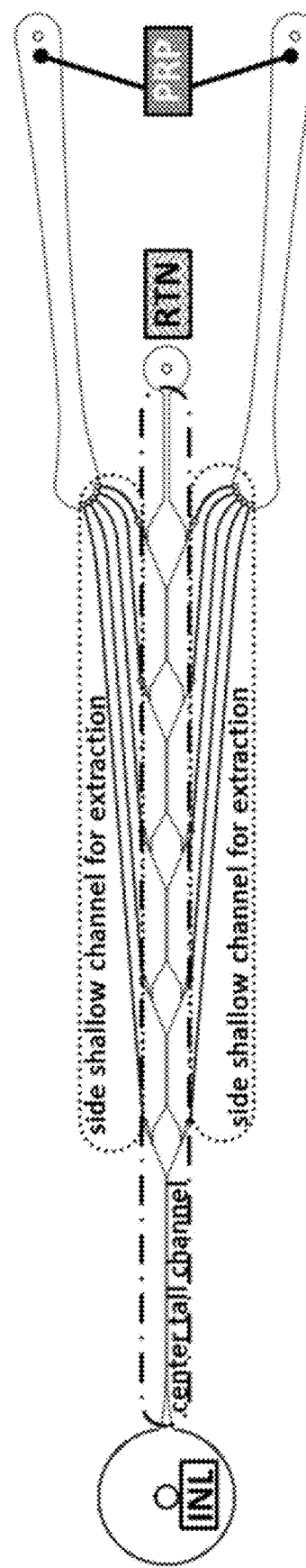
FIG. 15A includes a schematic that shows each branch contains five serial expansion sections from the inlet INL to the return RTN or platelet rich plasma PRP.
Figure 15B:
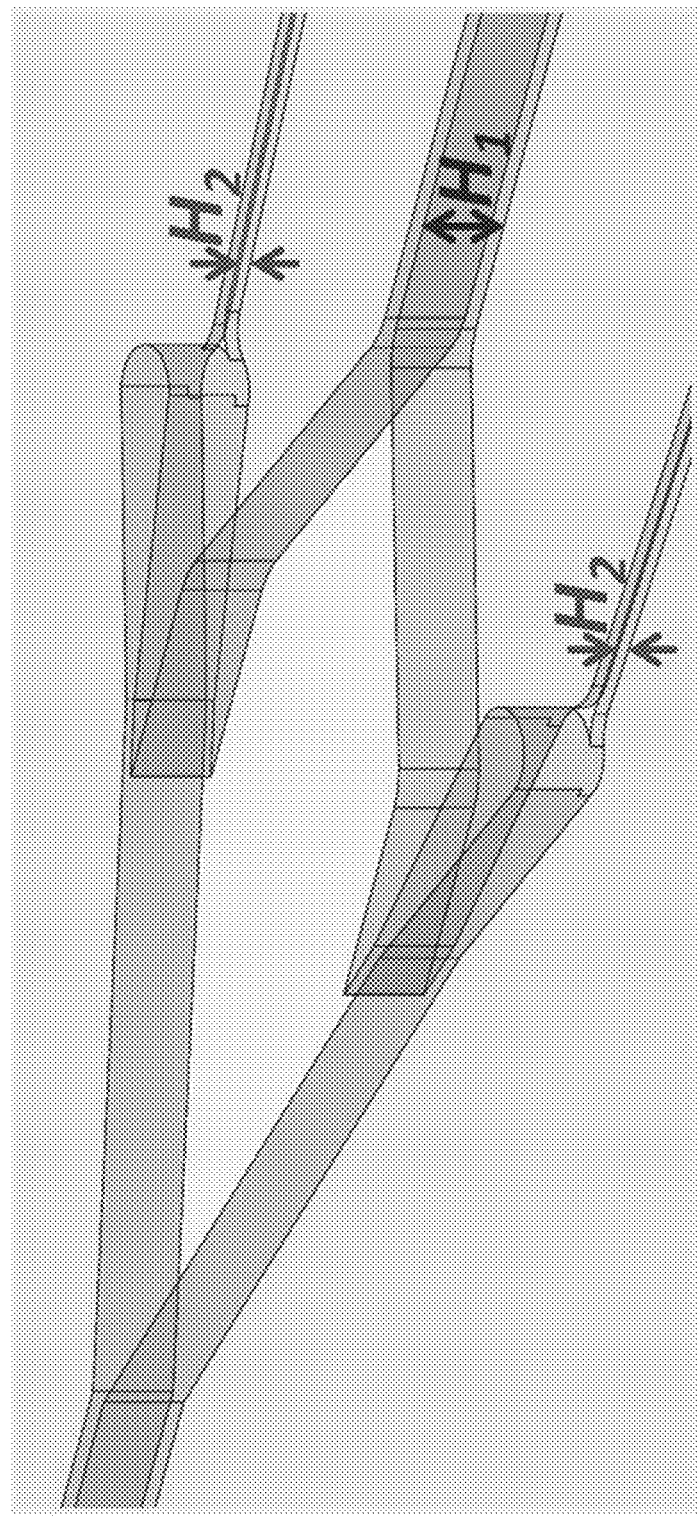
FIG. 15B includes a schematic that shows the side extraction channels were designed with a shallower depth compared with the main microfluidic channel along the centerline.

Each branch contains five serial expansion sections as shown in FIG. 15A. Under the interaction of hydrodynamic wall lift force, abundant and deformable red blood cells (RBCs) migrated to the channel core in the constricted focusing channel and collected by the main microfluidic channel along the centerline. The plasma and platelets (PLTs) were expelled by the RBC core and marginated near the channel walls. The plasma and PLTs were collected by the side extraction channels at each expansion section, which were in turn connected to common reservoirs on either side of the central channel. The common extraction reservoir was designed with large cross-section, 500×120 μm, W×H to ensure a negligible fluidic resistance. The side extraction channels were designed with a shallower depth compared with the main microfluidic channel along the centerline as shown in FIG. 15B. Two-layer design enabled the design to avoid using long meandering high aspect ratio fluidic resistance channels. Instead, the extraction channels were designed to be much shorter and shallower. By design, each microfluidic cartridge was able to sustain a throughput rate of >10 mL/min without leakage. To ensure optimized sorting performance, the desired flow rate split was calculated and designed based on the fluidic resistance balance at each splitting arm of each expansion section. The "EXTX"/"RTN" outlet volume ratio at each expansion section was designed to range from 1:30 to 1:42, resulting in overall volume ratio split of 1:3.

One additional advantage of the two-layer design, is that the heights of the layers can be independently varied to achieve different extraction volumes. Through this, system can switch the operational mode from collecting platelet-rich plasma (PRP) from whole blood to collecting platelet-poor plasma (PPP) from PRP allowing the system to produce platelet concentrate (PC) by fabricating devices with different height combinations.

Figure 16A:
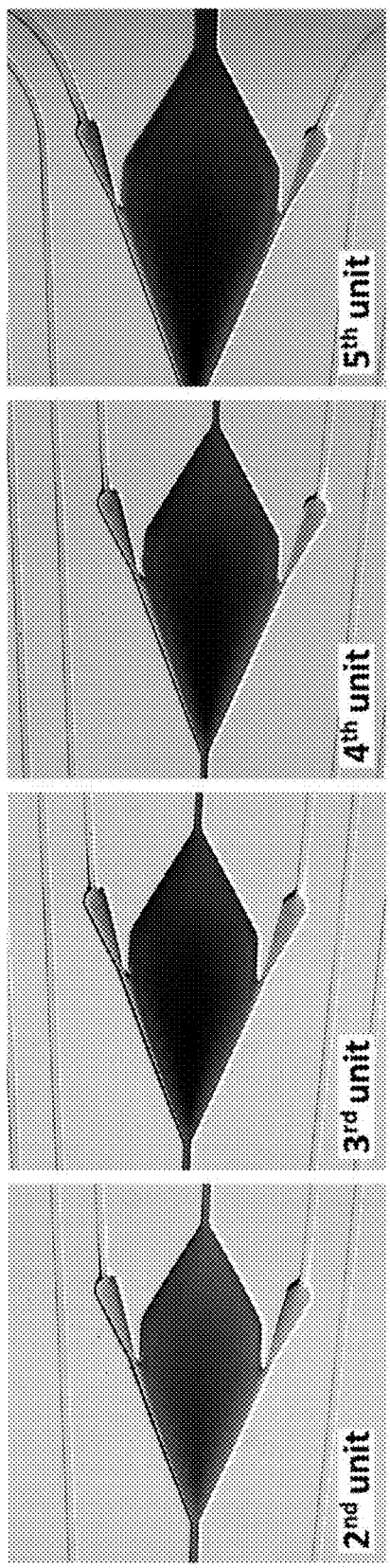
FIG. 16A shows RBC flow trajectories in real-time were imaged under an optical microscope at different locations of the device at one branch.
Figure 16B:
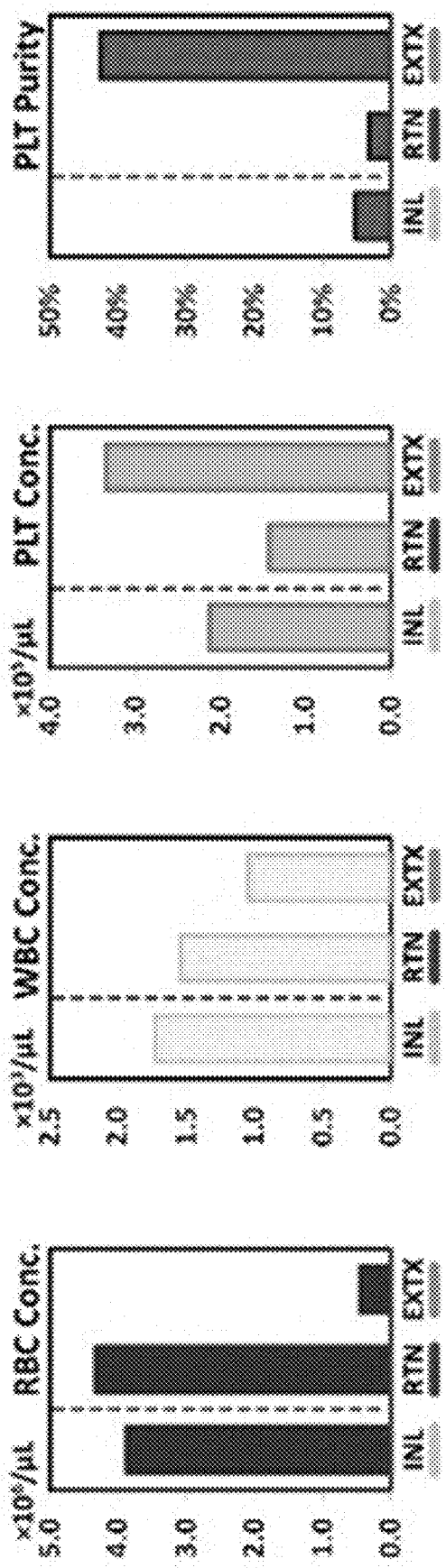
FIG. 16B shows the sorting performance data.

The system used SU-8 silicon masters to cast PDMS substrates for the multi-layer microfluidic cartridges. The cartridge inlet was connected to syringe pump for testing. Prior to blood sorting, the devices were primed by flowing buffer solutions at 5 mL/min in the main fluidic channels and at 1 mL/min in the side extraction channels (back-flow). Freshly collected blood from a donor by venipuncture infused with 10% ACD-A was used as the inlet sample. After priming the device with buffer, we collected WB samples in 50 mL syringe and used a syringe pump to infuse to each device at 20 mL/min for 2.5 min. No leakage was encountered for each device. The RBC flow trajectories in real-time were imaged under an optical microscope at different locations of the device at one branch as shown in FIG. 16A. Most RBCs were collected along the main microfluidic channel for all expansion sections. A small portion of RBCs were collected to the side extraction channels. The processed samples were cell counted under an epifluorescence microscope. The RBC portion was counted in bright field imaging with 100× dilution in 10% ACD 1×PBS buffer. The PLT and WBC portion were counted with 10× dilution in 10% ACD 1×PBS buffer with Calcein AM staining. Cells with >4 μm diameter were counted as WBCs, while cells with diameter <4 μm were counted as PLTs. Sorting performance is shown in FIG. 16B. Multi-layer devices resulted in RBC concentration discard of >97% and PLT purity ~40% in the "EXTX" samples in single pass operation. The PLT purity was about 40% with the PLT extraction of ~30%.

Collection Manifold for Platelet Extraction Plates

Figure 17:
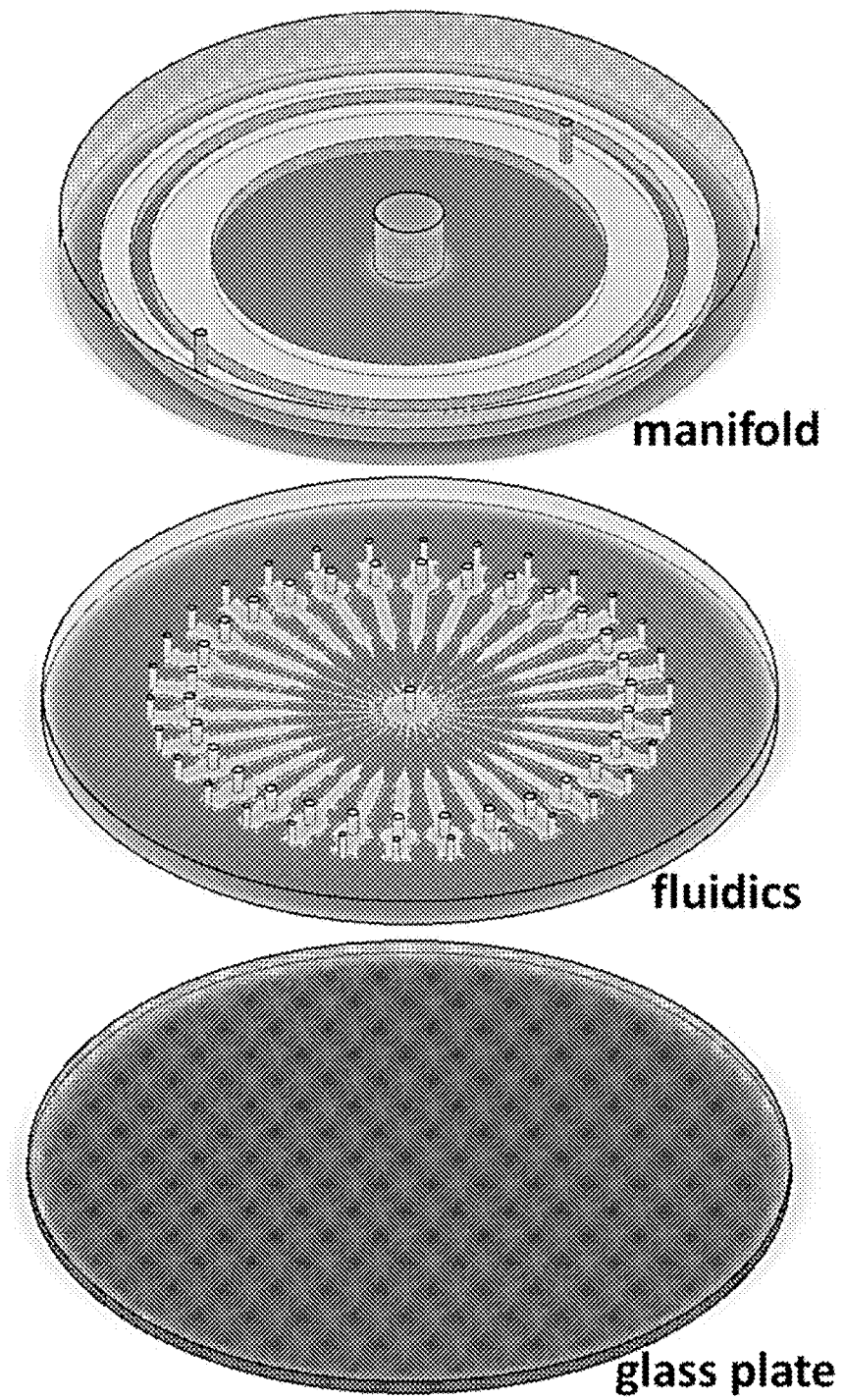
FIG. 17 shows a PDMS manifold that connects all common outlets from the fluidics layer of the microfluidic platelet extraction plates.

The PDMS manifold can be configured as in FIG. 17, which connects all common outlets from the fluidics layer of the microfluidic platelet extraction plates to avoid extensive use of connection tubing. The PDMS manifold consisted of two annular rings. The inner ring connected all "RTN" outlets from the fluidics layer to one common outlet. The outlet ring connected all EXTX outlets from the fluidics layer to another common outlet. These inlets and common outlets were connected to syringe, reservoirs, or other fluidic components through a single Tygon™ tubing (0.050" ID, 0.090" OD). The center inlet was inserted with a Luer fitting, which can be detached from the microfluidic platelet extraction plate. The PDMS manifold can be repeatedly casted with micro-machining of a thin polycarbonate mold. After fabricating the microfluidic platelet extraction plate, the PDMS manifold was aligned and capped on top of the fluidic layer after cleaning and surface activation with oxygen plasma treatment, followed with bonding on a hot plate. A glass plate was bonded using a hot-plate on the bottom of the microfluidic platelet extraction plate after cleaning and surface activation with oxygen plasma treatment. A $\frac{1}{16}$" barbed straight connector was inserted into each outlet on the manifold and a Luer connector was inserted into inlet port. The entire microfluidic assembly was encapsulated with another PDMS stack on a petri dish to sustain high pressure build-up near the inlet location for higher flow rate operation.

Automated Dual-Pump Operation of the Platelet Apheresis Cartridges

Figure 18A:
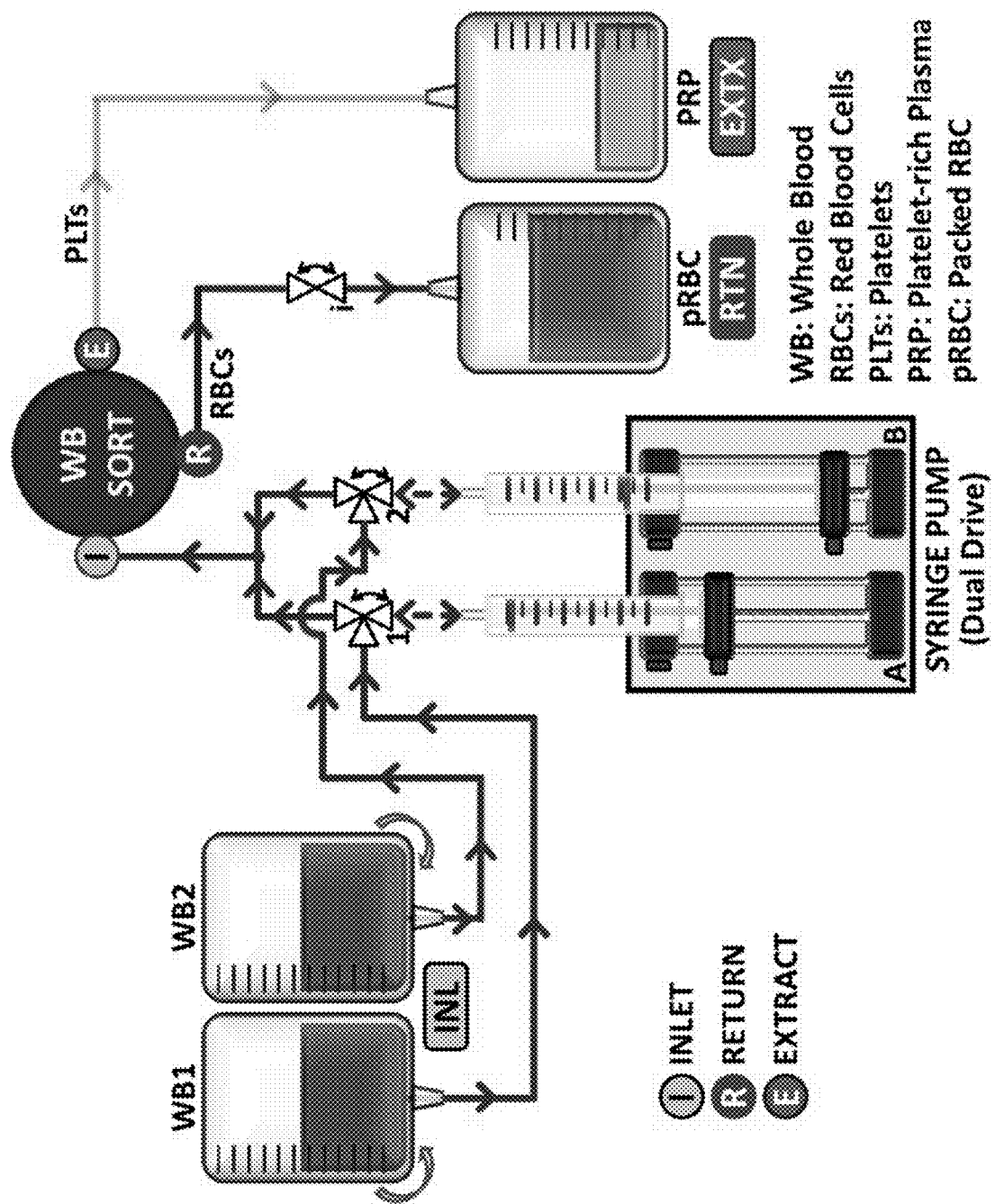
FIG. 18A shows the platelet apheresis cartridges can be operated using dual syringe pumps.

In some embodiments, the platelet apheresis cartridges were operated using dual syringe pump as in FIG. 18A. At any given time, one syringe is operated in the infuse mode to provide blood to the microfluidic device, and the other syringe is operated in the withdraw mode to pull blood from the whole blood input reservoir. When the infusing syringe is emptied out, the valves connected to the syringes are actuated such that the infusing syringe switches to the withdraw mode and the withdrawing syringe switches to the infuse mode. The process is repeated throughout the apheresis operation. The valve actuation time is of the order of 1 sec causing minimal disruption in the flow to the device. 3D-printed valve actuation fixtures controlled via a bread-board controller is utilized for automated operation of the valves. The bread-board controller is based on the Arduino Uno microcontroller and includes a MotorShield capable of driving multiple rotational actuators. Custom-designed 3D printed parts are fabricated that enclose the three-way valves as well as provide connectivity to the rotational actuator. The automated setup can be utilized to process large blood volumes (~1-1.5 L).

The valve actuation steps for the different processing steps: priming, and running, are as shown in FIG. 18B. The priming steps sequences consist of: filling the syringes with 10 mL of saline, priming the RETURN arm of the fluidic cartridge, and priming the EXTRACT arm of the fluidic cartridge. The running steps consist of: withdrawing WB in one syringe of the pump from the INL reservoir, infusing WB from the filled syringe while simultaneously withdrawing blood into the empty syringe, repeating the preceding step as needed, and finally infusing WB out from the filled syringe.

In some embodiments, a portable platelet apheresis system can include: a whole blood inlet configured to receive whole blood from a whole blood source; an anticoagulant source containing an anticoagulant; a mixer fluidly coupled with the whole blood inlet and anticoagulant source and configured to mix the whole blood and the anticoagulant; and a microfluidic cartridge fluidly coupled with an outlet of the mixer. The microfluidic cartridge includes a whole blood sorter. The whole blood sorter has a whole blood sorter microfluidic network that includes: a sorter constricted region having a first cross-sectional dimension; a sorter expansion region having a second cross-sectional dimension that is larger than the first cross-sectional dimension; at least one sorter side channel formed into a side of the sorter expansion region; and at least one sorter outlet that is downstream or medial from the at least one side channel. A platelet poor outlet is fluidly coupled with the at least one sorter outlet. A platelet concentrator outlet is fluidly coupled with the at least one sorter side channel.

In some embodiments a portable platelet apheresis system can include a microfluidic cartridge fluidly coupled with an outlet of the mixer, wherein the microfluidic cartridge includes a whole blood sorter and a platelet concentrator downstream from the whole blood sorter. The whole blood sorter has a whole blood sorter microfluidic network that includes: a sorter constricted region having a first cross-sectional dimension; a sorter expansion region having a second cross-sectional dimension that is larger than the first cross-sectional dimension; at least one sorter side channel formed into a side of the sorter expansion region; and at least one sorter outlet that is downstream or medial from the at least one side channel. The platelet concentrator has a platelet concentrator microfluidic network that includes: a concentrator constricted region having a third cross-sectional dimension that is fluidly coupled with the at least one sorter side channel; a concentrator expansion region having a fourth cross-sectional dimension that is larger than the third cross-sectional dimension, the concentrator expansion region being downstream from the concentrator constricted region; at least one concentrator side channel formed into a side of the concentrator expansion region; and at least one concentrator outlet that is downstream or medial from the at least one side channel. A platelet poor outlet is fluidly coupled with the at least one sorter outlet and/or the at least one concentrator side channel A platelet concentrator outlet is fluidly coupled with the at least one concentrator outlet (e.g., downstream, medial or central from the concentrator side channel).

In some embodiments, a portable platelet apheresis system can include: a microfluidic network fluidly coupled with an outlet of the mixer, wherein the microfluidic network includes a whole blood sorter network and a platelet concentrator network downstream from the whole blood sorter. The whole blood sorter microfluidic network includes: a sorter constricted region having a first cross-sectional dimension; a sorter expansion region having a second cross-sectional dimension that is larger than the first cross-sectional dimension; at least one sorter side channel formed into a side of the sorter expansion region; and at least one sorter outlet that is downstream or medial from the at least one side channel. The platelet concentrator microfluidic network that includes: a concentrator constricted region having a third cross-sectional dimension; a concentrator expansion region having a fourth cross-sectional dimension that is larger than the third cross-sectional dimension; at least one concentrator side channel formed into a side of the concentrator expansion region; and at least one concentrator outlet that is downstream or medial from the at least one side channel. A platelet poor outlet is fluidly coupled with the at least one sorter outlet and/or the at least one concentrator side channel. A platelet concentrator outlet is fluidly coupled with the at least one concentrator outlet that is downstream or medial or central from the side channel. In some aspects, the sorter microfluidic network and platelet concentrator microfluidic network are in the same cartridge. In some aspects, the sorter microfluidic network and platelet concentrator microfluidic network are in different cartridges. In some aspects, the sorter microfluidic network is in a sorter body of the cartridge and the platelet concentrator microfluidic network are in a concentrator body of the same cartridge.

In some embodiments, the sorter microfluidic network is in a first body of the cartridge and the platelet concentrator microfluidic network are in a second body of the same cartridge. The cartridge includes an intermediate body with microfluidic channels that fluidly couple the sorter microfluidic network with the concentrator microfluidic network.

In some embodiments, a portable platelet apheresis system can include a pump fluidly coupled to the mixer and microfluidic network. A micro-controller can be operably coupled to a pump that is fluidly coupled to the mixer and microfluidic network.

In some embodiments, a casing (e.g., portable, like a hard brief case, pelican case, etc.) is adapted for containing the components of the portable platelet apheresis system. The casing can be a housing having a port adapted for removably receiving the cartridge. The casing can also contain a flowmeter fluidly coupled with the pump and the cartridge. In some aspects, the micro-controller is configured to receive flow date from the flowmeter and provide flow rate instruction data to the pump to obtain a desired flow rate. In some aspects, the micro-controller is configured to receive flow date from the flowmeter and change flow rate instruction data based on the flow data, and provide changed flow rate instruction data to the pump to obtain a changed flow rate.

In some embodiments, the portable platelet apheresis system can include: a series of whole blood sorter microfluidic networks in series; and at least one concentrator microfluidic network downstream from at least one of the whole blood sorter microfluidic networks. In some aspects, the system can include: a series of whole blood sorter microfluidic networks in series; and at least one concentrator microfluidic network downstream from each of the whole blood sorter microfluidic networks. In some aspects, a saline source fluidly coupled with an inlet of the sorter constricted region of a first whole blood sorter microfluidic network. In some aspects, the system includes a series of whole blood sorter microfluidic networks in series and one concentrator microfluidic network downstream from a last whole blood sorter microfluidic network of the series. In some aspects, the cartridge is configured as a disc cartridge.

In some embodiments, a whole blood sorter can include a whole blood sorter microfluidic network that includes: an inlet; a sorter constricted region having a first cross-sectional dimension downstream of the inlet; a sorter expansion region having a second cross-sectional dimension that is larger than the first cross-sectional dimension and that is downstream of the sorter constricted region; at least one sorter side channel formed into a side of the sorter expansion region; and at least one sorter outlet that is downstream or medial from the at least one side channel. In some aspects the inlet is configured to include whole blood during use. The expansion region includes platelets preferentially in side lateral regions thereof and includes white blood cells and red blood cells preferentially in a medial region between the two side lateral regions during use. The at least one sorter side channel includes a majority of separated platelets and a minority of separated white blood cells and separated red blood cells during use. The at least one sorter outlet includes a majority of separated white blood cells and separated red blood cells and a minority of separated platelets during use.

In some embodiments, the whole blood sorter can include two sorter side channels formed into opposite sides of the sorter expansion region and at least one sorter outlet are arranged laterally between the two sorter side channels. In some aspects, an inlet narrowing taper region is upstream of the sorter constricted region. In some aspects, the sorter expansion region includes an expanding section with a narrow inlet and expanded outlet. In some aspects, the sorter expansion region includes an expanding section with a narrow inlet and expanded outlet upstream of an expanded conduit section. In some aspects, the sorter expansion region includes an expanding section with a narrow inlet and expanded outlet upstream of an expanded conduit section has a longitudinal cross-section or longitudinal/latitudinal plane with a shape of a triangle.

In some embodiments, the whole blood sorter can include two sorter side channels formed into opposite sides of the sorter expansion region and a plurality of sorter outlets all arranged medially or centrally between the two sorter side channels. In some aspects, two sorter side channels are formed into opposite sides of the sorter expansion region and are outer channels, and a plurality of sorter outlets are all arranged between the two sorter side channels and are thereby considered inner channels between the two outer sorter side channels. In some aspects, the two sorter side channels are at opposite corners of the triangle shaped expansion region with the plurality of sorter outlets all arranged at the base of the triangle shaped expansion region between the opposite corners.

In some embodiments, a platelet concentrator can include a platelet concentrator microfluidic network that includes: an inlet; a concentrator constricted region having a first cross-sectional dimension downstream of the inlet; a concentrator expansion region having a second cross-sectional dimension that is larger than the first cross-sectional dimension and that is downstream of the concentrator constricted region; at least one concentrated side channel formed into a side of the concentrator expansion region; and at least one concentrator outlet that is downstream or medial or central from the at least one side channel. The inlet is configured to have platelet rich plasma when used. The expansion region is configured to include plasma preferentially in side lateral regions thereof and include platelets preferentially in a medial region between the two side lateral regions during use. The at least one concentrator side channel includes a majority of plasma and a minority of separated platelets during use. The at least one concentrator outlet includes a majority of separated platelets during use.

In some embodiments, two sorter concentrator channels are formed into opposite sides of the concentrator expansion region and at least one concentrator outlet is arranged between the two concentrator side channels. In some aspects, an inlet narrowing taper region is upstream of the concentrator constricted region. In some aspects, the concentrator expansion region includes an expanding section with a narrow inlet and expanded outlet. In some aspects, the concentrator expansion region includes an expanding section with a narrow inlet and expanded outlet upstream of an expanded conduit section. In some aspects, the concentrator expansion region includes an expanding section with a narrow inlet and expanded outlet upstream of an expanded conduit section has a longitudinal cross-section or longitudinal/latitudinal plane with a shape of a triangle or rectangle.

In some embodiments, two concentrator side channels are formed into opposite sides of the concentrator expansion region and a plurality of concentrator outlets are all arranged centrally or medially between the two concentrator side channels. The plurality of concentrator outlets can be arranged laterally with respect to each other.

In some embodiments, two concentrator side channels are formed into opposite sides of the concentrator expansion region and are outer channels, and a plurality of concentrator outlets are all arranged between the two concentrator side channels so as to be medial or central with respect to the two concentrator side channels. The concentrator outlets can be the inner channels that are medial or central or otherwise between the two outer channels. In some aspects, the two concentrator side channels are at opposite corners of the triangle or rectangle shaped expansion region with the plurality of concentrator outlets all arranged at the base of the triangle or rectangle shaped expansion region between the opposite corners. In some aspects, the concentrator outlets are the penultimate outlets when the side channels are the ultimate outlets.

In some embodiments, a method of separating platelets from whole blood can include: providing the portable platelet system of one of the embodiments; introducing whole blood into the whole blood inlet; mixing the whole blood with the anticoagulant; introducing the whole blood from the mixer into the whole blood sorter; collecting separated platelets from the at least one sorter side channel and/or the at least one concentrator outlet; and collecting separated white blood cells and red blood cells from the at least one sorter outlet. The methods can include collecting platelet poor plasma from the at least one concentrator side channel. The methods can also include controlling a flow rate through the microfluidic networks.

In some embodiments, a method of separating platelets from whole blood can include: proving the whole blood sorter of one of the embodiments; introducing whole blood into the sorter constricted region; flowing the whole blood through the sorter expansion region so as to preferentially distribute platelets at lateral sides and preferentially distribute white blood cells and red blood cells medially between the lateral sides; collecting separated platelets from the at least one sorter side channel; and collecting separated white blood cells and red blood cells from the at least one sorter outlet.

A method of separating platelets from platelet rich plasma can include: proving the platelet concentrator of one of the embodiments; introducing platelet rich plasma into the concentrator constricted region; flowing the platelet rich plasma through the constrictor expansion region so as to preferentially distribute platelets away from the lateral sides and preferentially distribute platelets medially between the lateral sides (flowing the platelet rich plasma through the constrictor expansion region so as to preferentially distribute platelets in a region that is laterally away from a centerline and medially away from the lateral sides); collecting separated plasma from the at least one concentrator side channel; and collecting separated platelets from the at least one concentrator outlet.

The methods can be performed as described herein, such as in the examples.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In one embodiment, the present methods can include aspects performed on a computing system. As such, the computing system can include a memory device that has the computer-executable instructions for performing the method. The computer-executable instructions can be part of a computer program product that includes one or more algorithms for performing any of the methods of any of the claims.

In one embodiment, any of the operations, processes, methods, or steps described herein can be implemented as computer-readable instructions stored on a computer-readable medium. The computer-readable instructions can be executed by a processor of a wide range of computing systems from desktop computing systems, portable computing systems, tablet computing systems, hand-held computing systems as well as network elements, base stations, femtocells, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be affected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Figure 13:
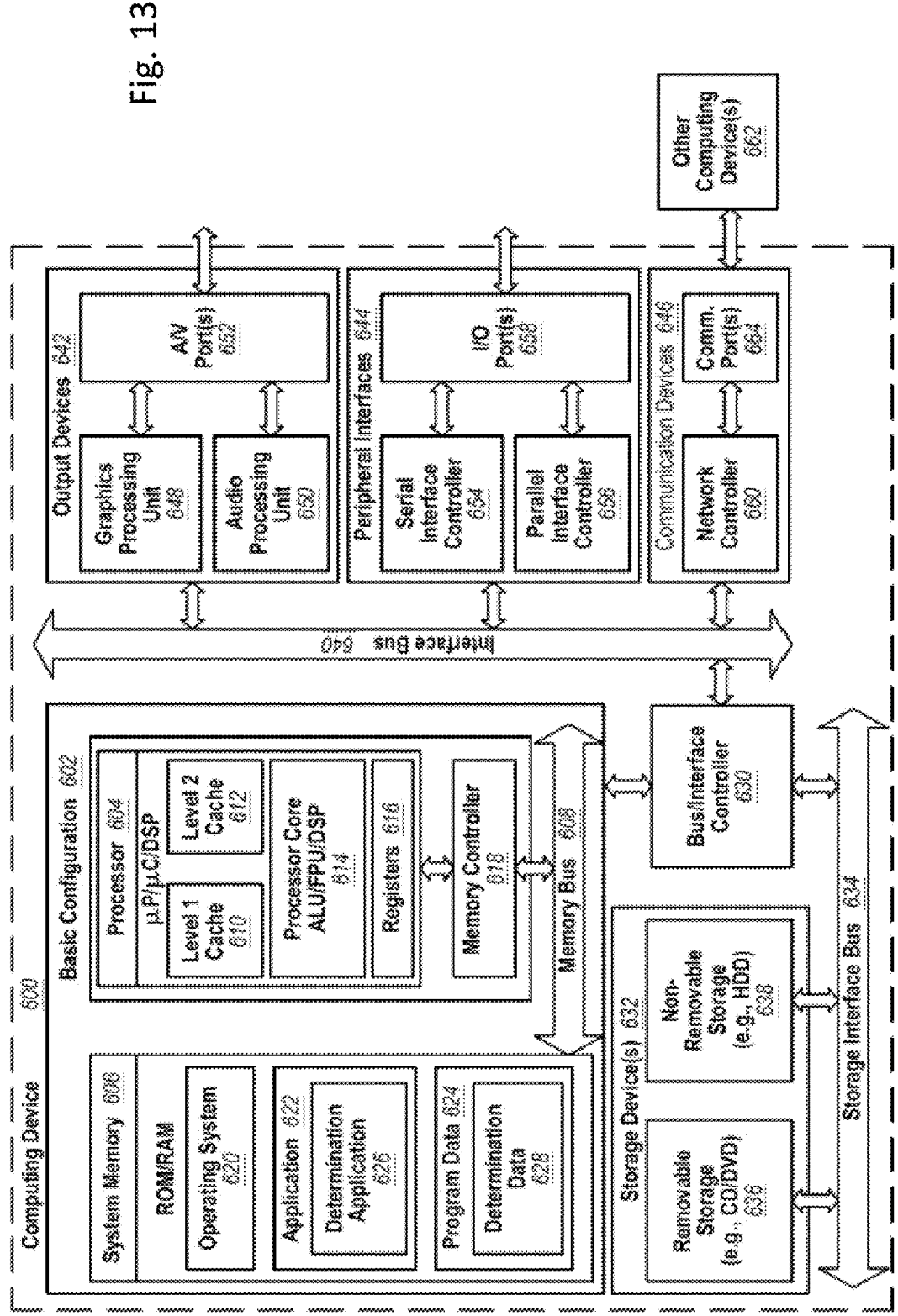
FIG. 13 includes a schematic diagram of a computing device that can operate as a controller of the systems described herein.

FIG. 13 shows an example computing device 600 that is arranged to perform any of the computing methods described herein. In a very basic configuration 602, computing device 600 generally includes one or more processors 604 and a system memory 606. A memory bus 608 may be used for communicating between processor 604 and system memory 606.

Depending on the desired configuration, processor 604 may be of any type including but not limited to a microprocessor (µP), a microcontroller (µC), a digital signal processor (DSP), or any combination thereof. Processor 604 may include one or more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations memory controller 618 may be an internal part of processor 604.

Depending on the desired configuration, system memory 606 may be of any type including but not limited to volatile memory (such as RAM), non-volatile memory (such as ROM, flash memory, etc.) or any combination thereof. System memory 606 may include an operating system 620, one or more applications 622, and program data 624. Application 622 may include a determination application 626 that is arranged to perform the functions as described herein including those described with respect to methods described herein. Program Data 624 may include determination information 628 that may be useful for analyzing the contamination characteristics provided by the sensor unit 240. In some embodiments, application 622 may be arranged to operate with program data 624 on operating system 620 such that the work performed by untrusted computing nodes can be verified as described herein. This described basic configuration 602 is illustrated in FIG. 6 by those components within the inner dashed line.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 600 may also be implemented as a personal computer including both laptop computer and non-laptop computer configurations. The computing device 600 can also be any type of network computing device. The computing device 600 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "module" or "component" can refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modulates running on a computing system.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

The invention claimed is:

1. A portable platelet apheresis system comprising:
    a whole blood inlet configured to receive whole blood from a whole blood source;
    an anticoagulant source containing an anticoagulant;
    a mixer fluidly coupled with the whole blood inlet and anticoagulant source and configured to mix the whole blood and the anticoagulant;
    a whole blood sorter network that includes a whole blood sorter microfluidic network having:
        a sorter constricted region having a first cross-sectional dimension;
        a sorter expansion region having a second cross-sectional dimension that is larger than the first cross-sectional dimension;
        at least one sorter side channel formed into a side of the sorter expansion region; and
        at least one sorter outlet that is downstream or medial from the at least one sorter side channel;
    at least one platelet concentrator comprising a platelet concentrator microfluidic network configured for concentrating platelets from plasma, each platelet concentrator comprising an inlet fluidly coupled with the at least one sorter side channel;
    a platelet poor outlet positioned to receive a platelet poor fraction from each of the at least one sorter outlets; and
    a platelet concentrator outlet positioned to receive a concentrated platelet fraction from the platelet concentrator microfluidic network of each of the platelet concentrators.

2. The portable platelet apheresis system of claim 1, further comprising the at least one platelet concentrator, wherein each platelet concentrator has the platelet concentrator microfluidic network that includes:
    a concentrator constricted region having a third cross-sectional dimension that is fluidly coupled with the at least one sorter side channel;
    a concentrator expansion region having a fourth cross-sectional dimension that is larger than the third cross-sectional dimension, the concentrator expansion region being downstream from the concentrator constricted region;
    at least one concentrator side channel formed into a side of the concentrator expansion region; and
    at least one concentrator outlet that is downstream or medial from the at least one concentrator side channel.

3. The portable platelet apheresis system of claim 1, wherein:
    the platelet poor outlet is fluidly coupled with the at least one sorter outlet and/or the at least one concentrator side channel; and/or
    the platelet concentrator outlet is fluidly coupled with the at least one concentrator outlet.

4. The portable platelet apheresis system of claim 1, wherein the whole blood sorter is included on a microfluidic cartridge, which can be removably fluidly coupled with the outlet of the mixer, wherein the microfluidic cartridge includes the whole blood sorter, wherein the whole blood sorter has the whole blood sorter microfluidic network.

5. The portable platelet apheresis system of claim 1, further comprising the at least one platelet concentrator, wherein each platelet concentrator has the platelet concentrator microfluidic network that includes:
    a concentrator constricted region having a third cross-sectional dimension;
    a concentrator expansion region having a fourth cross-sectional dimension that is larger than the third cross-sectional dimension;
    at least one concentrator side channel formed into a side of the concentrator expansion region;
    at least one concentrator outlet that is downstream or medial from the at least one concentrator side channel;
    a platelet poor outlet fluidly coupled with the at least one sorter outlet and/or the at least one concentrator side channel; and
    a platelet concentrator outlet fluidly coupled with the at least one concentrator side channel.

6. The portable platelet apheresis system of claim 5, wherein the whole blood sorter microfluidic network and platelet concentrator microfluidic network are in the same cartridge or different cartridges.

7. The portable platelet apheresis system of claim 6, wherein the whole blood sorter microfluidic network is in a sorter body of the cartridge and the platelet concentrator microfluidic network are in a concentrator body of the same cartridge.

8. The portable platelet apheresis system of claim 6, wherein the sorter microfluidic network is in a first body of the cartridge and the platelet concentrator microfluidic network are in a second body of the same cartridge, and the cartridge includes an intermediate body with microfluidic channels that fluidly couple the whole blood sorter microfluidic network with the platelet concentrator microfluidic network.

9. The portable platelet apheresis system of claim 6, further comprising:
a casing containing the components of the portable platelet apheresis system;
a pump fluidly coupled to the mixer and microfluidic network
a port in the casing adapted for removably receiving the cartridge;
a flowmeter fluidly coupled with the pump and the cartridge; and
micro-controller that is configured to receive flow rate from the flowmeter and provide flow rate instruction data to the pump to obtain a desired flow rate.

10. The portable platelet apheresis system of claim 5, further comprising:
a series of whole blood sorter microfluidic networks in series; and
at least one platelet concentrator microfluidic network downstream from at least one of the whole blood sorter microfluidic networks.

11. The portable platelet apheresis system of claim 5, further comprising:
a series of whole blood sorter microfluidic networks in series; and
at least one platelet concentrator microfluidic network downstream from each of the whole blood sorter microfluidic networks.

12. The portable platelet apheresis system of claim 5, further comprising a saline source fluidly coupled with an inlet of the sorter constricted region of a first whole blood sorter microfluidic network.

13. The portable platelet apheresis system of claim 5, further comprising:
a series of whole blood sorter microfluidic networks in series; and
one platelet concentrator microfluidic network downstream from a last whole blood sorter microfluidic network of the series.

14. The portable platelet apheresis system of claim 1, further comprising at least one of:
a pump fluidly coupled to the mixer and microfluidic network;
a micro-controller operably coupled to the pump that is fluidly coupled to the mixer and microfluidic network.

15. The portable platelet apheresis system of claim 1 comprising a first whole blood sorter comprising:
a first whole blood sorter microfluidic network that includes:
an inlet;
a first sorter constricted region having a first cross-sectional dimension downstream of the inlet;
a first sorter expansion region having a second cross-sectional dimension that is larger than the first cross-sectional dimension and that is downstream of the first sorter constricted region;
at least one first sorter side channel formed into a side of the first sorter expansion region; and
at least one first sorter outlet that is downstream or medial from the at least one first sorter side channel.

16. The portable platelet apheresis system of claim 15, further comprising:
two first sorter side channels formed into opposite sides of the first sorter expansion region; and
at least one first sorter outlet are arranged laterally between the two first sorter side channels.

17. The portable platelet apheresis system of claim 15, further comprising an inlet narrowing taper region upstream of the first sorter constricted region.

18. The portable platelet apheresis system of claim 15, wherein the first sorter expansion region includes an expanding section with a narrow inlet and expanded outlet.

19. The portable platelet apheresis system of claim 15, wherein the first sorter expansion region includes an expanding section with a narrow inlet and expanded outlet upstream of an expanded conduit section.

20. The portable platelet apheresis system of claim 15, further comprising two first sorter side channels formed into opposite sides of the first sorter expansion region and being outer channels, and a plurality of first sorter outlets all arranged laterally between the two first sorter side channels and being inner channels between the two outer channels.

21. The portable platelet apheresis system of claim 20, wherein the two first sorter side channels are at opposite corners of the triangle shaped expansion region with the plurality of first sorter outlets all arranged at the base of a triangle shaped expansion region between the opposite corners.

22. The portable platelet apheresis system of claim 1 comprising a first platelet concentrator comprising:
a platelet concentrator microfluidic network that includes:
an inlet;
a first concentrator constricted region having a first cross-sectional dimension downstream of the inlet;
a first concentrator expansion region having a second cross-sectional dimension that is larger than the first cross-sectional dimension and that is downstream of the first concentrator constricted region;
at least one first concentrator side channel formed into a side of the first concentrator expansion region; and
at least one first concentrator outlet that is downstream or medial from the at least one first concentrator side channel.

23. The portable platelet apheresis system of claim 22, further comprising:
two first sorter concentrator channels formed into opposite sides of the first concentrator expansion region; and
at least one first concentrator outlet are arranged laterally between the two first concentrator side channels.

24. The portable platelet apheresis system of claim 22, further comprising an inlet narrowing taper region upstream of the first concentrator constricted region.

25. The portable platelet apheresis system of claim 22, wherein the first concentrator expansion region includes an expanding section with a narrow inlet and expanded outlet upstream of an expanded conduit section.

26. The portable platelet apheresis system of claim 22, further comprising two first concentrator side channels formed into opposite sides of the first concentrator expansion region and being outer channels, and a plurality of concentrator outlets all arranged laterally between two first concentrator side channels and being inner channels between the two outer channels.

27. The portable platelet apheresis system of claim 26, wherein the two first concentrator side channels are at opposite corners of the triangle or rectangle shaped expansion region with the plurality of concentrator outlets all arranged at the base of a triangle or rectangle shaped expansion region between the opposite corners.

28. A method of separating platelets from whole blood comprising:
   providing the portable platelet apheresis system of claim 5;
   introducing whole blood into the whole blood inlet;
   mixing the whole blood with the anticoagulant;
   introducing the whole blood from the mixer into the whole blood sorter;
   passing platelets in plasma through the at least one sorter side channel and the at least one platelet concentrator;
   collecting separated platelets from the at least one sorter side channel through the at least one platelet concentrator to obtain concentrated platelets in plasma; and
   collecting separated white blood cells and red blood cells from the at least one sorter outlet.

29. The method of claim 28, further comprising collecting platelet poor plasma from the at least one concentrator side channel.

30. The method of claim 28, further comprising controlling a flow rate through the whole blood sorter microfluidic network and platelet concentrator microfluidic network.

\* \* \* \* \*